United States Patent
Shadduck

(10) Patent No.: US 6,669,694 B2
(45) Date of Patent: Dec. 30, 2003

(54) MEDICAL INSTRUMENTS AND TECHNIQUES FOR HIGHLY-LOCALIZED THERMALLY-MEDIATED THERAPIES

(76) Inventor: John H. Shadduck, 1490 Vistazo West, Tiburon, CA (US) 94920

( * ) Notice: Subject to any disclaimer, the term of this patent is extended or adjusted under 35 U.S.C. 154(b) by 0 days.

(21) Appl. No.: 10/017,582

(22) Filed: Dec. 7, 2001

(65) Prior Publication Data

US 2002/0082667 A1 Jun. 27, 2002

Related U.S. Application Data

(60) Provisional application No. 60/254,487, filed on Dec. 9, 2000, and provisional application No. 60/230,556, filed on Sep. 5, 2000.

(51) Int. Cl.$^7$ ............................................. A61B 18/18
(52) U.S. Cl. ............................................. 606/41; 606/28
(58) Field of Search ............................. 606/41, 27, 28, 606/48–50; 604/21, 22, 114; 607/101–105

(56) References Cited

U.S. PATENT DOCUMENTS

| | | | | |
|---|---|---|---|---|
| 5,554,172 A | * | 9/1996 | Horner et al. ................. | 607/88 |
| 5,683,366 A | * | 11/1997 | Eggers et al. ................ | 604/114 |
| 5,697,882 A | * | 12/1997 | Eggers et al. ................ | 604/114 |
| 5,944,715 A | * | 8/1999 | Goble et al. ................... | 606/41 |
| 6,032,674 A | * | 3/2000 | Eggers et al. ................ | 128/898 |
| 6,047,700 A | * | 4/2000 | Eggers et al. ............... | 128/898 |
| 6,224,592 B1 | * | 5/2001 | Eggers et al. ................. | 606/32 |
| 6,261,286 B1 | * | 7/2001 | Goble et al. ................... | 606/34 |

* cited by examiner

Primary Examiner—Michael Peffley

(57) ABSTRACT

This invention relates a novel surgical device scalable to small dimensions for thermally-mediated treatments or thermoplasties of targeted tissue volumes. An exemplary embodiment is adapted for shrinking, sealing or welding tissue. The instruments and techniques utilize a thermal energy delivery means, for example an electrical energy source, to instantly vaporize a biocompatible fluid media within an electrically insulated instrument body. The altered media is characterized by a (i) a high heat content, and (ii) a high exit velocity from the working end both of which characteristics are controlled to hydrate tissue and at the same time denature proteins to shrink, seal, weld or cause any other thermally-mediated treatment of an engaged tissue volume—while causing limited collateral thermal damage and while totally eliminating electrical current flow the engaged tissue volume. The system can further utilize a piezoelectric material that carries fluid channels to apply compressive forces to eject the gas media from the working end of allow a lesser electrical energy requirement to convert a liquid to a gas and to increase media exit pressure.

17 Claims, 24 Drawing Sheets

MEDICAL INSTRUMENTS AND TECHNIQUES FOR HIGHLY-LOCALIZED THERMALLY-MEDIATED THERAPIES

CROSS-REFERENCE TO RELATED APPLICATIONS

This application claims benefit of Provisional U.S. patent application Ser. No. 60/254,487 filed Dec. 9, 2000 (Docket No. S-DESC-059) having the same title as this disclosure, which is incorporated herein by reference. This application also is related to Provisional U.S. patent Ser. No. 60/230,556 filed Sep. 5, 2000 (now abandoned) which is incorporated herein by this reference.

FIELD OF THE INVENTION

This invention relates to a novel surgical device scalable to small dimensions for thermally-mediated treatments or thermoplasties of targeted tissue volumes. An exemplary embodiment is adapted for shrinking, sealing or welding tissue. The instrument and technique utilize electrical energy to instantly convert a biocompatible fluid media to a superheated media, perhaps a gas media, within an electrically insulated instrument working end. The altered media is characterized by a (i) a high heat content, and (ii) a high exit velocity from the working end's tissue engagement plane. Both of these characteristics are controlled to hydrate tissue while at the same time denaturing proteins to shrink, seal, weld or cause any other thermally-mediated treatment of an engaged tissue volume—and while causing limited collateral thermal damage and totally eliminating electrical current flow in the engaged tissue volume.

BACKGROUND OF THE INVENTION

Various types of laser and radiofrequency (Rf) surgical instruments have been developed for delivering thermal energy to tissue, for example to cause hemostasis, to weld tissue or to cause a thermoplastic remodeling of tissue. While such prior art forms of energy delivery work well for may applications, laser and Rf energy typically cannot cause highly localized thermal effects that are desirable in microsurgeries or other precision surgeries.

Laser and Rf energy applications cause thermal effects in tissue based on different principles. In general, the non-linear or non-uniform characteristics of tissue affect both laser and Rf energy distributions in tissue. For example, FIG. 1A shows a typical pattern of energy distribution and resultant thermal effects in a prior art laser irradiation of tissue. The cross-section of the energy emitter or emission is indicated at ee at the tissue interface wherein a fiber optic interfaces tissue of a light beam strikes the tissue. In the case of a suitable infrared laser emission, water in tissue comprises a chromophore to absorb photonic energy resulting in a thermal effect. The turbidity of tissue scatters photons, and the resulting thermal effect is indicated by arbitrary isotherms 100, 80 and 60 which for example indicate degrees in centigrade. FIG. 1A shows that tissue desiccation d at the surface will occur to prevent photon transmission after an certain interval of energy delivery. If the objective of the thermal therapy in FIG. 1A were to seal or weld tissue, which is assumed to require a threshold temperature of 80° C., it can be seen that deeper tissue indicated at b may not reach the threshold welding temperature before the tissue surface is desiccated. Further, it can be seen that collateral tissue indicated at c may be sealed or welded, even though such tissue is collateral to the cross-section of the energy emission ee.

FIG. 1B next shows a typical energy distribution pattern when using a prior art bi-polar Rf energy delivery. In this schematic illustration, the cross-section of the energy emitter is again indicated at ee which defines the interface between a tissue surface and the electrodes 4a and 4b. As the electrodes are energized from an electrical source, the current flows are in constant flux and flow through random paths of least resistant between the electrodes. The tissue is elevated in temperature by it resistance to current flow, resulting typically in tissue desiccation or charring d at the electrode-tissue interface. When tissue in contact with the electrode is entirely desiccated, the current flow between the electrodes terminates. As represented in FIG. 1B, thermal effects typically occur in regions of tissue (indicated at c) collateral to the targeted tissue between the electrodes. Further, the prior art Rf energy delivery of FIG. 1B causes stray Rf flow collateral tissues that may be undesirable.

What is needed is an instrument and technique (i) that can controllably deliver thermal energy to non-uniform tissue volumes; (i) that can shrink, seal or weld selected tissue volumes without desiccation or charring of proximate tissue layers; (iii) that can shrink, seal or weld a targeted tissue volume while preventing collateral thermal damage; and (iv) that does not cause stray Rf current flow in tissue.

SUMMARY OF THE INVENTION

The present invention is adapted to provide novel systems and techniques capable of controlled thermal energy delivery to localized tissue volumes, for example for sealing, welding or thermoplastic remodeling of tissue. Of particular interest, the system can create thermal welds or seals in a targeted tissue without the use of Rf current flow through the patient's body, which is typical in the prior art. The systems and techniques are particularly adapted for sealing or welding thick tissue and non-uniform tissue layers. The biological mechanisms underlying tissue fusion or welding are complex and are not fully understood. Application of thermal energy can be used to elevate tissue temperatures to the level that causes denaturation of proteins, which is a first step in tissue fusion. The terms fuse, weld and seal are used interchangeably herein, mean that a temperature-induced protein denaturation process causes such proteins (particularly various types of collagen), water and other tissue constituents to meld into a proteinaceous amalgam. Such a form of thermal biological glue occurs at temperatures ranging from about 65° C. to 100° C. Upon the cooling of tissue and subsequent healing of the treated tissue, the tissue is fused together or welded as the damaged proteins re-nature in a part of the body's wound healing process.

The probe of the present invention has a working end that defines a tissue-contacting surface or engagement plane with a plurality of media entrance ports that enter the engagement plane. A fluid media source is fluidly coupled to the media entrance ports by a fluid channel. Fluid vaporization means, for example comprising paired electrodes, are carried within the channel for converting the fluid media from a first liquid state to a second gas state—i.e., a flash vaporization means. The instrument and technique thus utilize electrical energy to convert the biocompatible fluid media to a superheated gas media that has a high heat content that enters the engagement plane at velocity and penetrates into the targeted tissue.

In a further embodiment of the invention, the tissue-contacting surface may carry components of a sensor system which together with a power controller can control the intervals of electrical discharges during a thermotherapy. For example, feedback circuitry for measuring temperatures at one or more temperature sensors may be provided. The power controller can also modulate and control voltage of the discharge to alter media exit velocity, all in order to achieve (or maintain) a particular parameter such as a particular temperature in tissue, an average of temperatures measured among multiple sensors, or a temperature profile (change in energy delivery over time).

The instrument and method of the invention advantageously cause thermal effects in tissue that do not rely applying an electrical field across the tissue to be treated.

The instrument and method of the invention advantageously cause thermal effects in tissue that do not rely delivering high-intensity laser energy to the targeted tissue.

The instrument and method of the invention creates thermal effects in targeted tissue that without causing tissue desiccation or surface carbonization common to electrosurgical modalities and laser irradiation modalities.

The instrument and method of the invention advantageously creates thermal effects in a targeted tissue volume with substantially controlled lateral margins between the treated tissue and untreated tissue.

The instrument and method of the invention creates thermal effects in targeted tissues that caused stray electrical current flow in the patient's body.

Additional advantages of the invention will be apparent from the following description, the accompanying drawings and the appended claims.

BRIEF DESCRIPTION OF THE DRAWINGS

FIG. 5A being a sectional illustration of the delivery of a fluid media to the working end, FIG. 5B being an illustration of electrical discharged induced flash vaporization of the contained fluid to thereby eject a superheated gas into the targeted tissue to cause a thermal weld.

DETAILED DESCRIPTION OF THE INVENTION

Figure 2A:
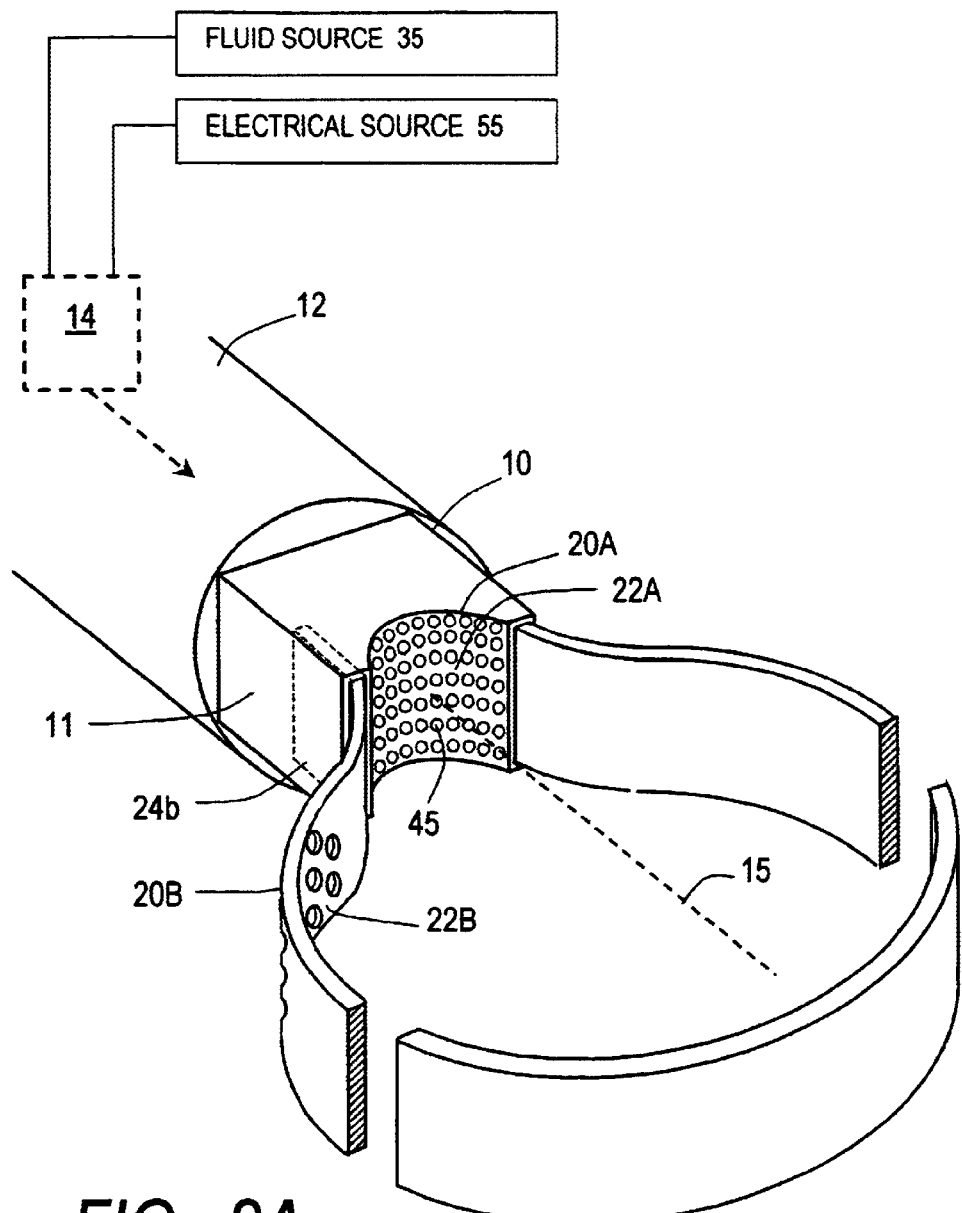
FIG. 2A is a perspective view of the working end of an exemplary Type "A" probe of the present invention with an openable-closable tissue engaging structure in a first open position.
Figure 2B:
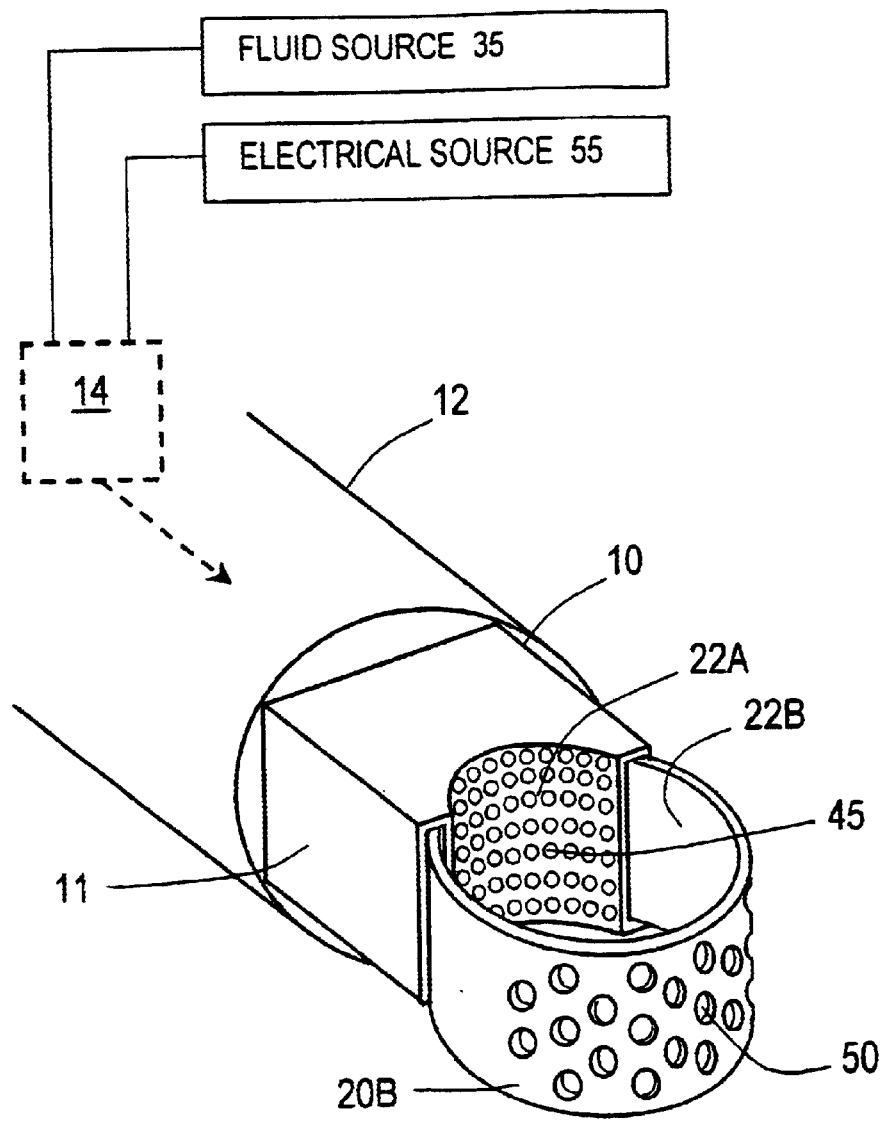
FIG. 2B is a perspective view similar to FIG. 2A probe of the present invention in a second closed position.
Figure 3:
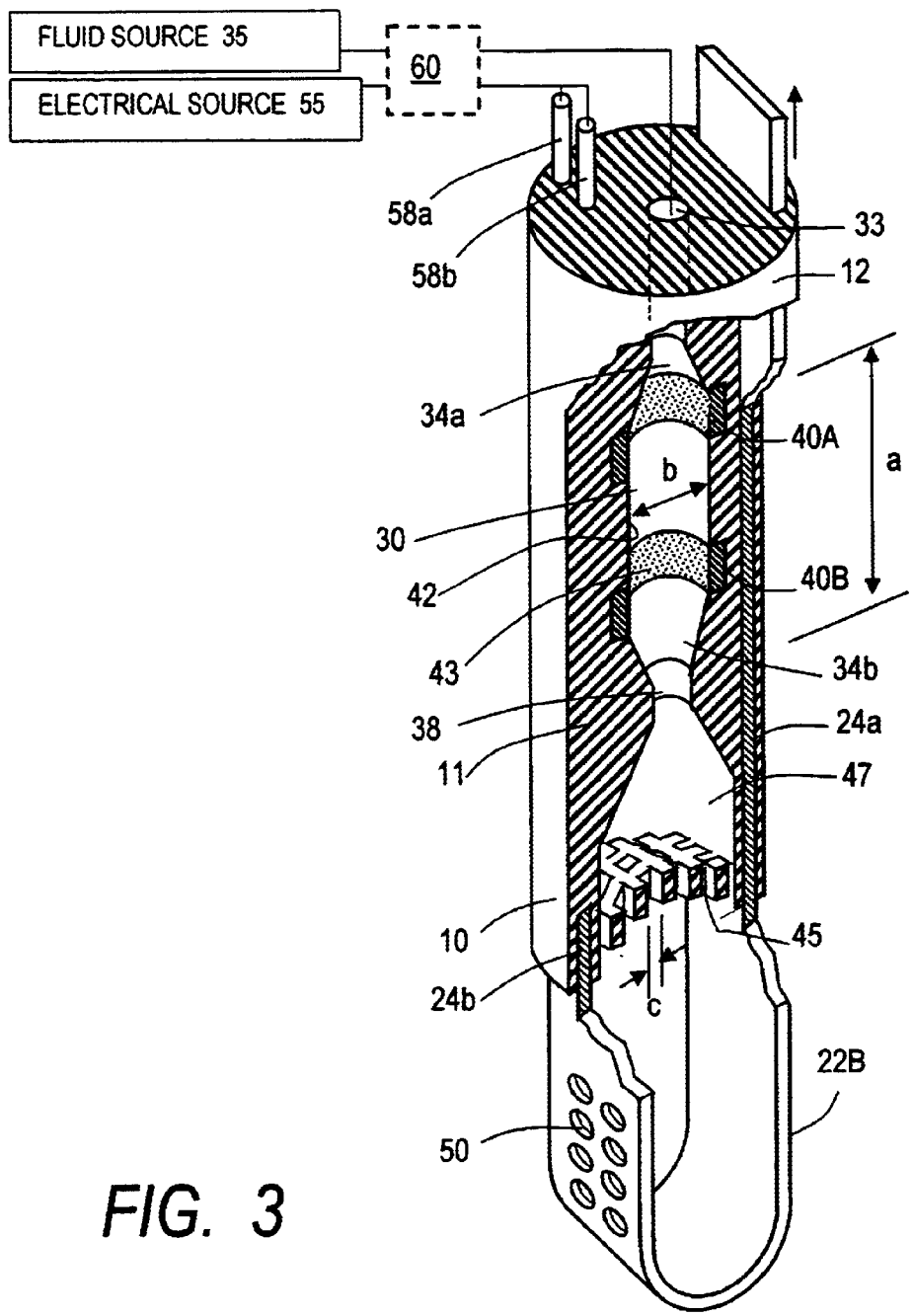
FIG. 3 is a cut-away view of the working end of FIGS. 2A–2B.

1. Type "A" System for Tissue Fusion. Referring to FIGS. 2A–2B and FIG. 3, the working end 10 of a Type "A" system 5 of the present invention is shown that is adapted for endoscopic procedures in which a tissue volume t targeted for fusion (a thermoplasty) can be captured by a loop structure. The working end 10 comprises a body 11 of insulator material (see FIG. 3) coupled to the distal end of introducer member 12 extending along axis 15. In this exemplary embodiment, the working end 10 has a generally cylindrical cross-section and is made of any suitable material such as plastic, ceramic, glass, metal or a combination thereof. The working end 10 is substantially small in diameter (e.g., 2 mm. to 5 mm.) and in this embodiment is coupled to an elongate flexible introducer member 12 to cooperate with a working channel in an endoscope. Alternatively, the working end 10 may be coupled to a rigid shaft member having a suitable 5 mm. to 10 mm. diameter to cooperate with a standard trocar sleeve for use in endoscopic procedures. A proximal handle portion 14 of the instrument indicated by the block diagram of FIG. 2A carries the various actuator mechanisms known in the art for actuating components of the instrument.

In FIGS. 2A–2B & 3, it can be seen that the working end 10 carries an openable and closeable structure for capturing tissue between a first tissue-engaging surface 20A and a second tissue-engaging surface 20B. In this exemplary embodiment, the working end 10 and first tissue-engaging surface 20A comprises a non-moving component indicated at 22A that is defined by the exposed distal end of body 11 of working end 10. The second tissue-engaging surface 20B is carried in a moving component that comprises a flexible loop structure indicated at 22B.

The second moving component or flexible loop 22B is actuatable by a slidable portion 24a of the loop that extends through a slot 25 in the working end to an actuator in the handle portion 14 as is known in the art (see FIG. 3). The other end 24b of the loop structure 22B is fixed in body 11.

While such an in-line (or axial) flexible slidable member is preferred as the tissue-capturing mechanism for a small diameter flexible catheter-type instrument, it should be appreciated that any openable and closable jaw structure known in the art falls within the scope of the invention, including forms of paired jaws with cam-surface actuation or conventional pin-type hinges and actuator mechanisms. FIG. 2A illustrates the first and second tissue-engaging surfaces 20A and 20B in a first spaced apart or open position. FIG. 2B show the first and second surfaces 20A and 20B moved toward a second closed position.

Now turning to the fluid-to-gas energy delivery means of the invention, referring to FIG. 3, it can be seen that the insulated or non-conductive body 11 of working end 10 carries an interior chamber indicated at 30 communicating with lumen 33 that are adapted for delivery and transient confinement of a fluid media m that flows into the chamber 30. The chamber 30 communicates via lumen 33 with a fluid media source 35 that may be remote from the device, or a fluid reservoir (coupled to a remote pressure source) carried within introducer 12 or carried within a handle portion 14. The term fluid or flowable media source 35 is defined to include a positive pressure inflow system which may be a syringe, an elevated remote fluid sac that relies on gravity, or any suitable pump-type pressure means known in the art. The fluid delivery lumen 33 transitions to chamber 30 at proximal end portion 34a thereof. The distal end portion 34b of chamber 30 has a reduced cross-section to (optionally) function as a jet or nozzle indicated at 38.

Of particular interest, still referring to FIG. 3, paired electrode elements 40A and 40B with exposed surfaces and that are spaced apart in surface 42 of the interior fluid confinement chamber 30. In this exemplary embodiment, the electrode elements 40A and 40B comprise (i) circumferential exposed surfaces of a conductive material (ii) positioned at opposing proximal and distal ends of interior chamber 30. It should be appreciated that the method of the invention of may utilize any suitable configuration of spaced apart electrodes about at least one confinement chamber 30 or lumen portion. For example, each electrode may be a singular projecting element that projects into the chamber. The exemplary embodiment of FIG. 3 shows an elongate chamber having an axial dimension indicated at a and diameter or cross-section indicated at b. The axial dimension may range from about 0.1 mm. to 20.0 mm. and may be singular or plural as described below. The diameter b may range from micron dimensions (e.g., 0.5 μm) for miniaturized instruments to a larger dimension (e.g., 5.0 mm) for larger instruments for causing the thermally induced fluid-to-gas transformation required to cause the novel energy-tissue interaction of the invention. The electrodes are of any suitable material such as aluminum, stainless steel, nickel titanium, platinum, gold, or copper. Each electrode surface preferably has a toothed surface texture indicated at 43 that includes hatching, projecting elements or surface asperities for better delivering high energy densities in the fluid proximate to the electrode. The electrical current to the working end 10 may be switched on and off by a foot pedal or any other suitable means such as a switch in handle 14.

FIG. 3 further shows that a preferred shape is formed into the tissue-engaging surface 20A to better perform the method of fusing tissue. As can be seen in FIGS. 2A and 3, the first tissue-engaging surface 20A is generally concave so as to be adapted to receive a greater tissue volume in the central portion of surface 20A. The second tissue-engaging surface 20B is flexible and naturally will be concave in the distal or opposite direction when tissue is engaged between surfaces 20A and 20B. This preferred shape structure allows for controllable compression of the thick targeted tissue volumes t centrally exposed to the energy delivery means and helps prevent conductance of thermal effects to collateral tissue regions ct (see FIG. 4B) and as will be described in greater detail below.

FIGS. 2A and 3 show that first tissue-engaging surface 20A defines an open grid structure of apertures or passageways indicated at 45 that pass therethrough. The apertures 45 may have any cross-sectional shape and linear or angular route through surface 20A with a sectional dimension c in this embodiment ranging upwards from micron dimensions (e.g., 0.5 μm) to about 2.0 mm. in a large surface 20A. The exemplary embodiment of FIG. 3 has an expanding cross-section transition chamber 47 proximate to the aperture grid that transitions between the distal end 34b of chamber 30 and the apertures 45. However, it should be appreciated that such a transition chamber 47 is optional and the terminal portion of chamber 30 may directly exit into a plurality of passageways that each communicate with an aperture 45 in the grid of the first engaging surface 20A. In a preferred embodiment, the second tissue-engaging surface 20B defines (optionally) a grid of apertures indicated at 50 that pass through the loop 22B. These apertures 50 may be any suitable dimension (cf apertures 45) and are adapted to generally oppose the first tissue-engaging surface 20A when the surfaces 20A and 20B are in the second closed position, as shown in FIG. 2B.

The electrodes 40A and 40B of working end 10 have opposing polarities and are coupled to electrical generator 55. FIG. 3 shows current-carrying wire leads 58a and 58b that are coupled to electrodes 40A and 40B and extend to electrical source 55 and controller 60. In a preferred embodiment of the invention, either tissue-engaging surface optionally includes a sensor 62 (or sensor array) that is in contact with the targeted tissue surface (see FIG. 2A). Such a sensor, for example a thermocouple known in the art, can measure temperature at the surface of the captured tissue. A thermocouple typically consists of paired dissimilar metals such as copper and constantan that form a T-type thermocouple. The sensor is coupled to controller 60 by a lead (not shown) and can be used to modulate or terminate power delivery as will be described next in the method of the invention.

Figure 4A:
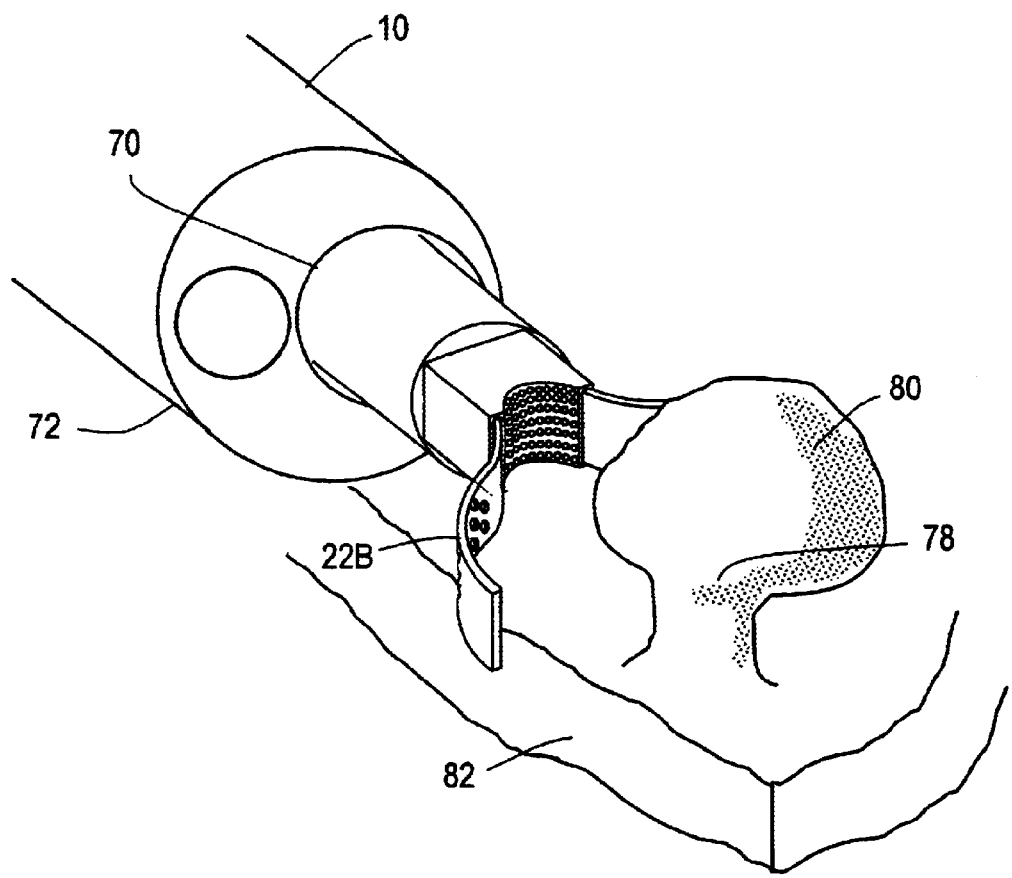
FIGS. 4A–4B are perspective views of the working end of FIG. 3 capturing a polyp in a patient's colon.
Figure 4B:
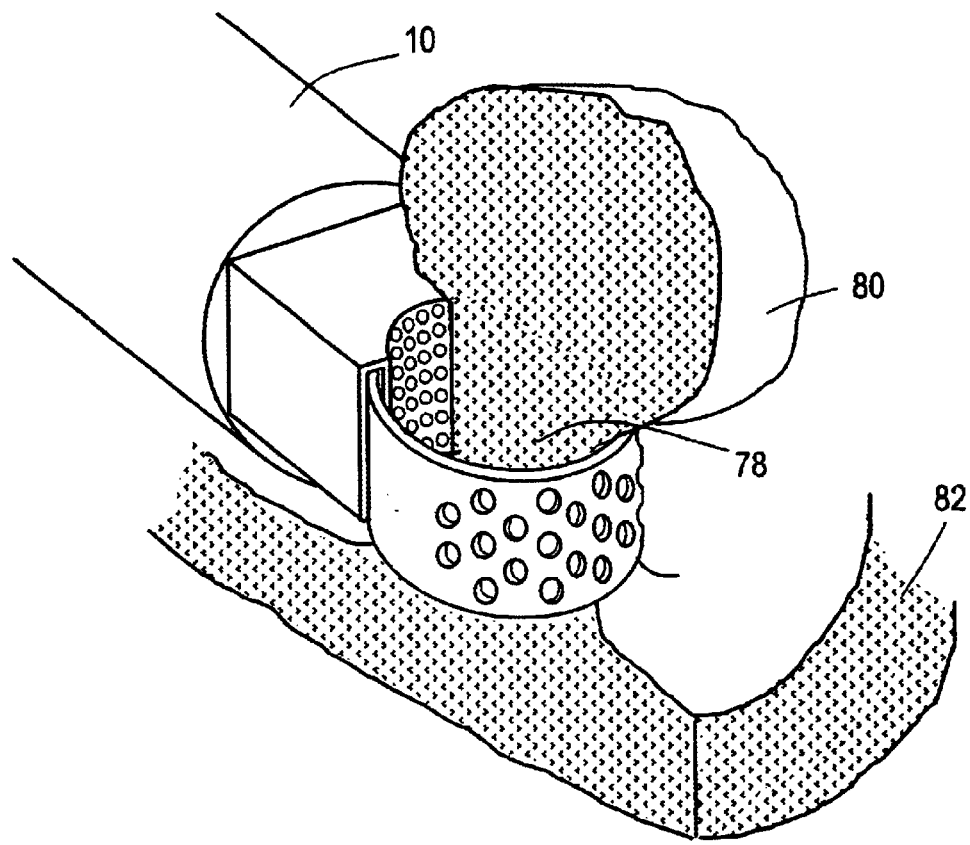

Operation and use of the working end of FIGS. 2A–2B and FIG. 3 in performing a method of the invention can be briefly described as follows in an endoscopic polyp removal procedure. FIGS. 4A–4B show working end 10 carried by an elongate catheter-type introducer member 12 and introduced through a working channel 70 of an endoscope 72 to a working space. In this case, the tissue t targeted for fusing or sealing is a medial portion 78 of a polyp 80 in a colon 82. It can be easily understood that the slidable movement of the loop member 22B can capture the polyp 80 in the device as shown in FIG. 4B after being lassoed. The objective of the tissue treatment is to (i) seal the medial portion of the polyp with the present invention, and thereafter (ii) utilize a separate cutting instrument to cut through the fused or sealed portion; and then (iii) retrieve the excised polyp for biopsy purposes.

Figure 5A:
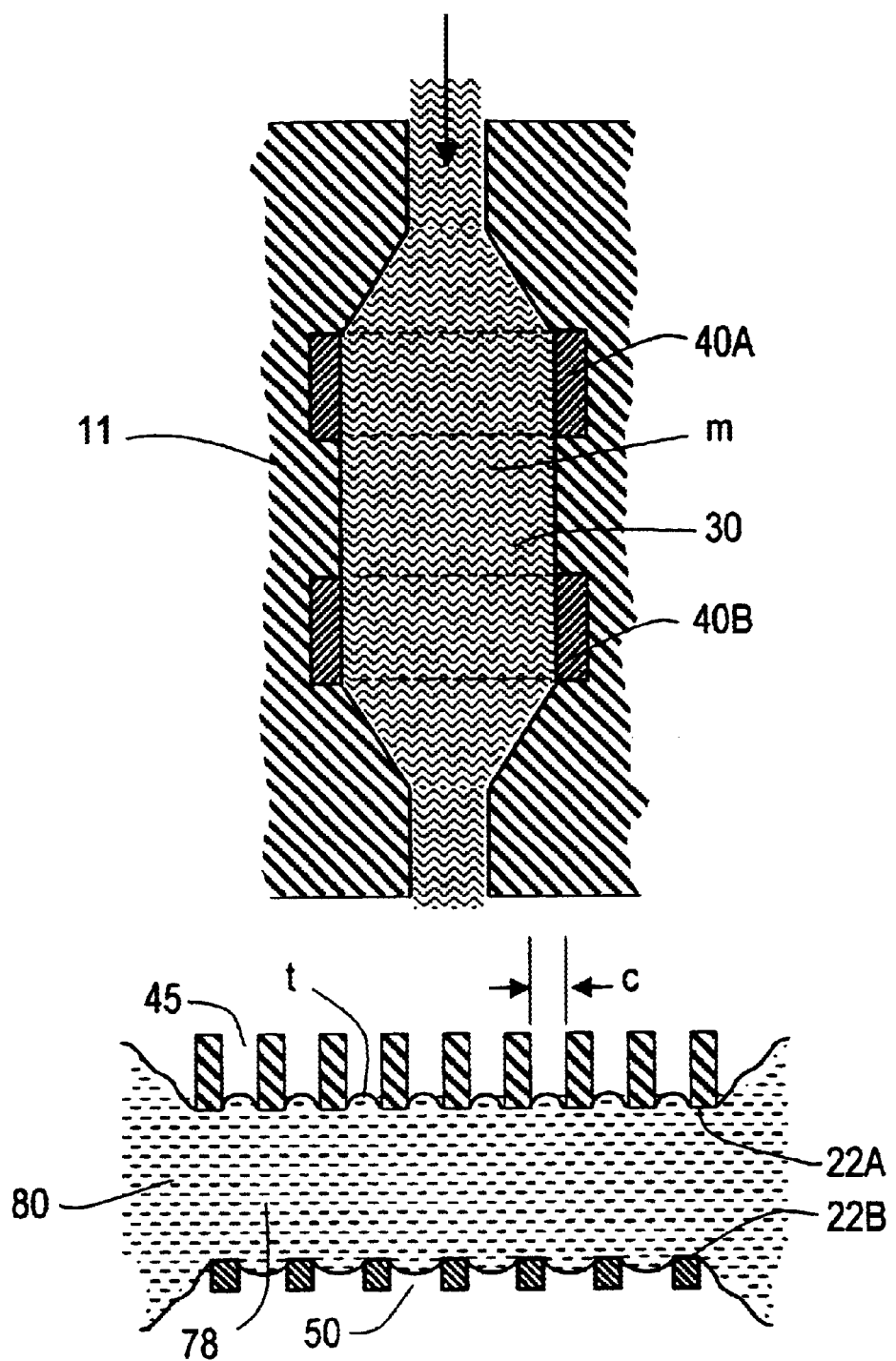
FIGS. 5A–5B are sectional schematic views of working end of FIG. 3 depicting, in sequence, the steps of a method of the present invention to seal or weld a targeted tissue volume.
Figure 5B:
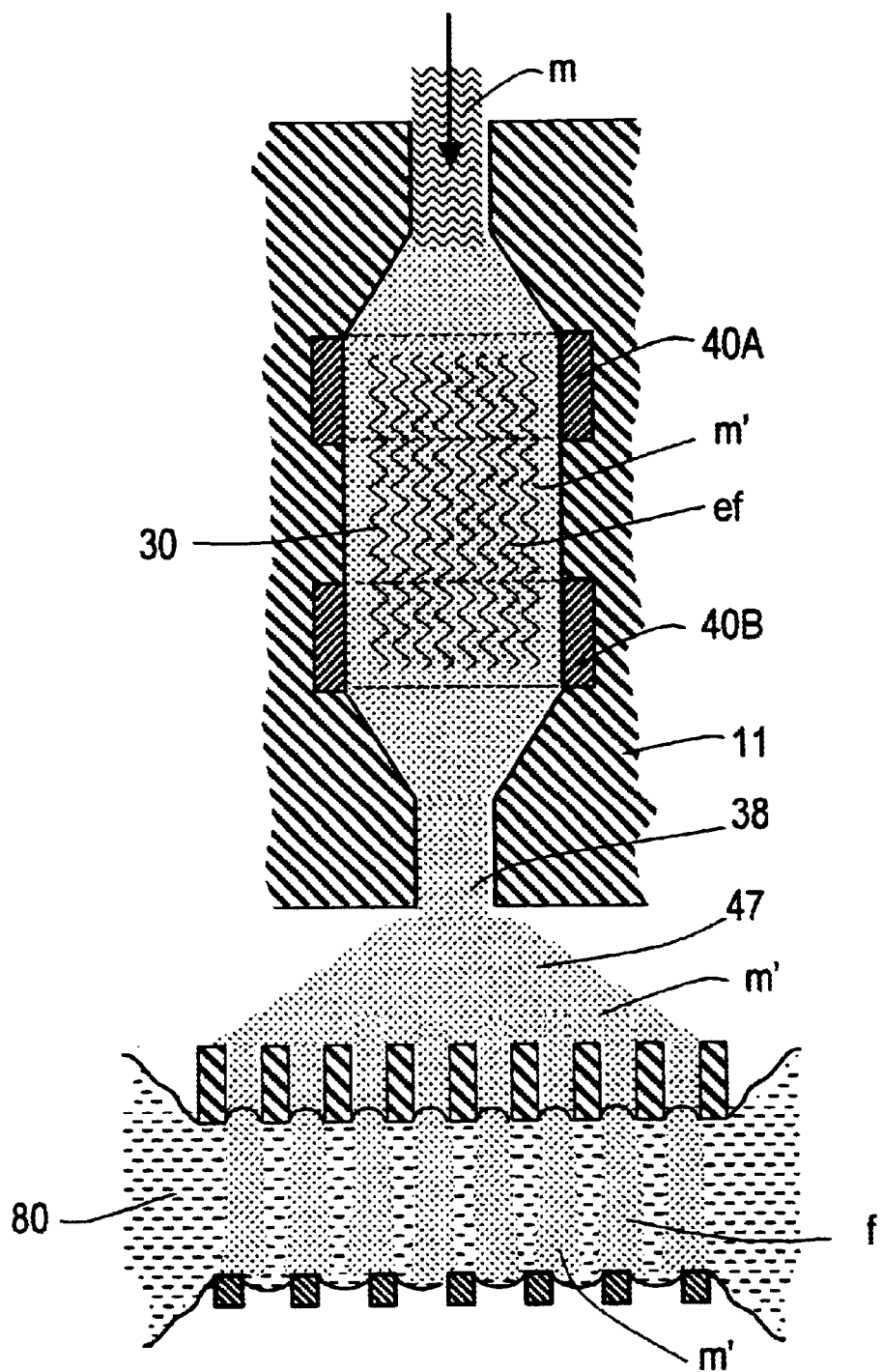

Now turning to FIGS. 5A–5B, two sequential schematic views of the working end engaging tissue t of the medial region of a polyp are provided to illustrate the energy-tissue interaction caused by the fluid-to-gas energy delivery means of the invention. FIG. 5A depicts an initial step of the method wherein the operator sends a signal to the controller 60 to delivery fluid media m (e.g., sterile water or saline solution) through lumen 33 into chamber 30. FIG. 5B depicts the next step of the method wherein the controller delivers an intense discharge of electrical energy to the paired electrode elements 40A and 40B within chamber 30 indicated by electric arc or electric field ef. The electrical discharge causes explosive vaporization of fluid media m (FIG. 5A) into a gas media indicated at m' (FIG. 5B). The greatly increased volume of gas media m' results in the gas being ejected from chamber 30 at high velocity through apertures 45 of the surface 20A and into the targeted tissue t. The fluid-to-gas conversion caused by the electrical discharge also heats the gas media m' to about 100° C. to deliver thermal effects into tissue t, or even through the targeted tissue t, as indicated graphically by the shaded regions of gas flow in FIG. 5B. Depending on the character of the introduced liquid media, the media can be altered from a first lesser temperature to a second greater temperature in the range of 100° to 400° C. It is believed that this form of gas media m' (or steam) can uniformly elevate the temperature of the captured tissue to the desired range of about 65° C. to 100° C very rapidly (i) to cause hydrothermal denaturation of proteins in the tissue, and (ii) to cause optimal fluid inter-mixing of tissue constituents that will result in an effective seal or weld. At the same time, as the heat of media m' is absorbed by the water in the targeted tissue, the media m' converts back to a fluid (e.g., water) thus hydrating the targeted tissue t. It is believed that such protein denaturation by hydrothermal effects differentiates this method of tissue fusion from all other forms of energy delivery, such as radiofrequency energy delivery. All other forms of energy delivery vaporize intra- and extracellular fluids and cause tissue desiccation, dehydration or charring which is undesirable for the intermixing of denatured tissue constituents into a proteinaceous amalgam.

The above electrical energy deliver step is repeated at a high repetition rate to cause a pulsed form of thermal energy delivery in the engaged tissue. The fluid media m inflow may be continuous or pulsed to substantially fill chamber 30 before an electrical discharge is caused therein. The repetition rate of electrical discharges may be from about 1 Hz to 1000 Hz. More preferably, the repetition rate is from about 10 Hz to 200 Hz. The selected repetition rate preferably provides an interval between electrical discharges that allows for thermal relaxation of tissue, that may range from about 10 ms to 500 ms. The electrical source or voltage source 55 may provide a voltage ranging between about 100 volts and 10,000 volts to cause instant vaporization of the volume of fluid media m captured between the electrode elements 40A and 40B. After a selected time interval of such energy application to tissue t, that may range from about 1 second to 30 seconds, and preferably from about 5 to 20 seconds, the engaged tissue will be contain a core region in which the tissue constituents are denatured and intermixed under relatively high compression between surfaces 20A and 20B. Upon disengagement and cooling of the targeted tissue t, the treated tissue will be fused or welded. Over time, the body's wound healing response will reconstitute the treated tissue with an intermixed collagenous volume or scar-like tissue.

An optional method of controlling the repetition rate of electrical discharges comprises the measurement of electrical characteristics of media m within the chamber 30 to insure that the chamber is filled with the fluid media at time of the electrical discharge. The electrical measurement then would send a control signal to the controller 60 to cause each electrical discharge. For example, the fluid media m can be provided with selected conductive compositions in solution therein. The controller 60 then can send a weak electrical current between the paired electrodes 40A and 40B and thereafter sense the change in an impedance level between the electrodes as the chamber 30 is filled with fluid to generate the control signal.

Figure 1A:
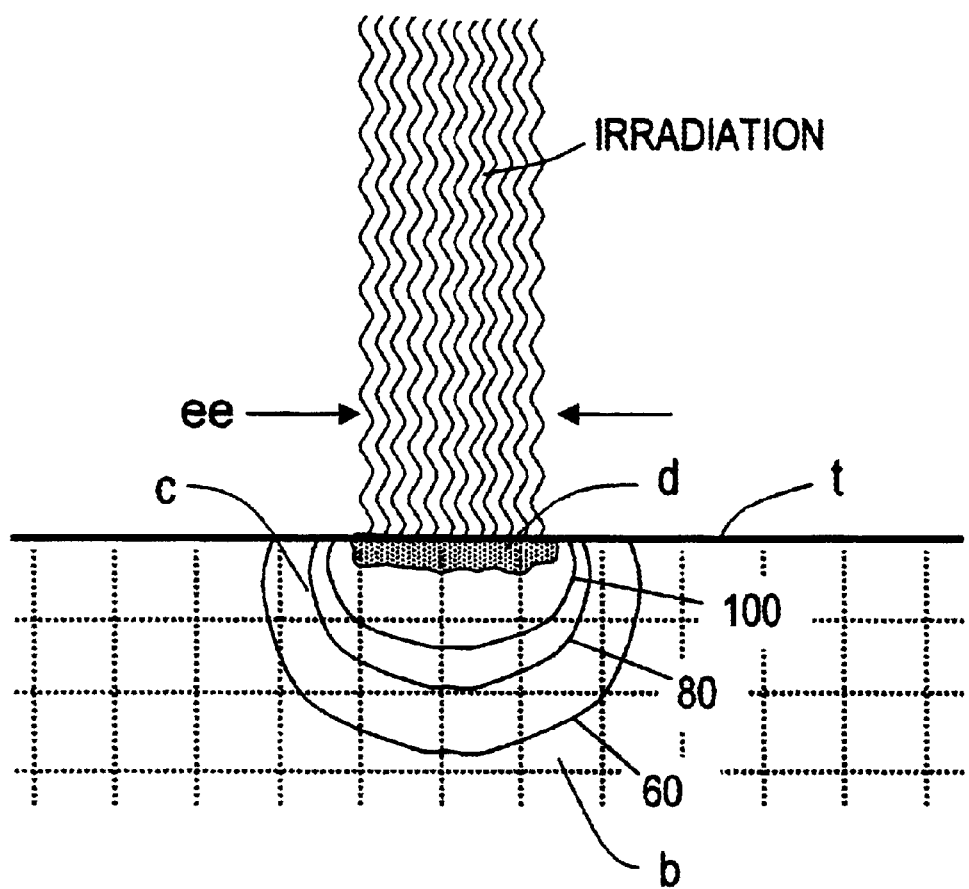
FIG. 1A is an illustration of a prior art laser-induced thermal weld effect in two approximated tissue layers.
Figure 1B:
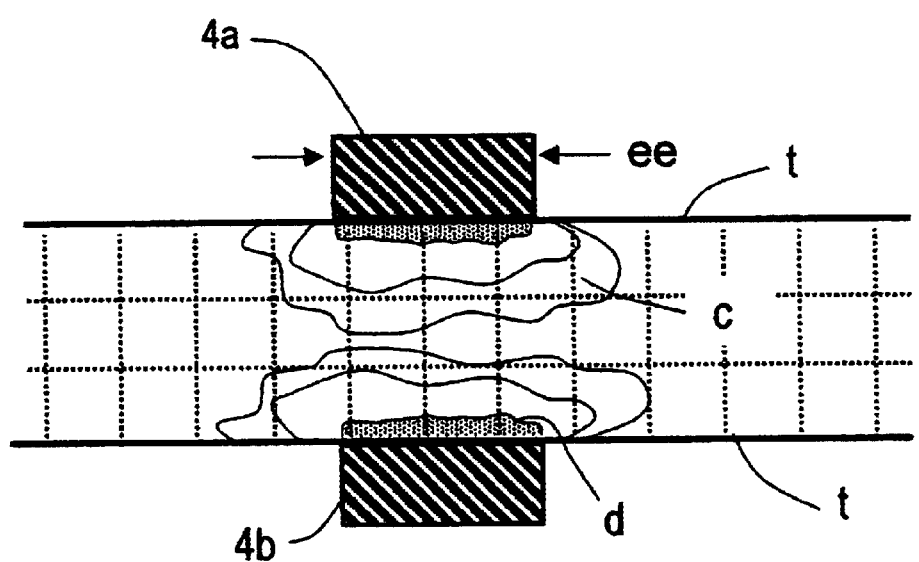
FIG. 1B is an illustration of a prior art radiofrequency energy induced thermal weld effect in two approximated tissue layers.

FIG. 5B further shows that the engaged tissue t of polyp 80 defines a medial portion that comprises the engaged tissue t and collateral tissue regions indicated at ct. It can be seen that the gas media m' will penetrate the medial engaged tissue t of the polyp but will not penetrate the collateral tissue ct not engaged between the engaging surfaces 20A and 20B. Of particular interest, the collateral tissue regions ct will thus not be elevated significantly in temperature and little collateral thermal damage will result. This desired lack of collateral thermal damage is to be contrasted with radiofrequency (Rf) energy delivery between one of more electrodes engaging the targeted tissue, in which Rf current will flow outwardly into and through the tissue regions ct and cause collateral thermal damage (see FIG. 1B). In the exemplary polyp removal procedure described herein, the invention's ability to limit collateral thermal damage is important for two reasons. First, it is important to maintain the portion of the polyp to be resected in a non-desiccated condition since it will be biopsied. Second, it is important to prevent thermal damage to the colon wall 94 at the base of the polyp 80, since any damage or perforation of the wall could result in serious complications. Still referring to FIG. 5C, it is estimated that temperature ranges will transition rapidly from a threshold level capable of denaturing proteins in the medial targeted tissue t, to subthreshold levels in the collateral tissue ct. In substantial part, the rapid temperature transition results from the transition between the compressed medial tissue t that in compressed between the engagement surfaces 20A and 20B and the collateral tissue volumes that are not engaged and compressed. It is the combination of tissue compression with the gas media induced elevation in temperature that can cause rapid denaturation of proteins in the targeted tissue t. The non-compressed collateral tissue ct will disperse any heat rapidly to limit collateral thermal damage. FIG. 5B further shows a resection line r along which the polyp can be transected with a separate instrument to leave a sealed margin at the base of the polyp that prevents any bleeding following the resection procedure.

Figure 6A:
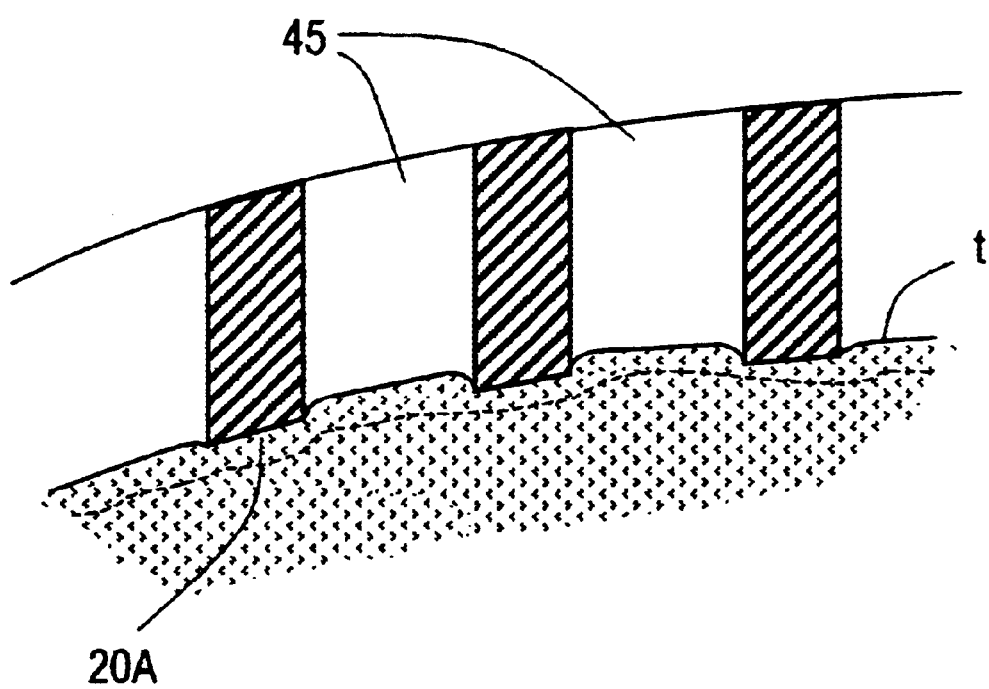
FIGS. 6A–6B are enlarged sectional views of apertures of the working end of FIG. 3 depicting a passive component of the present invention.
Figure 6B:
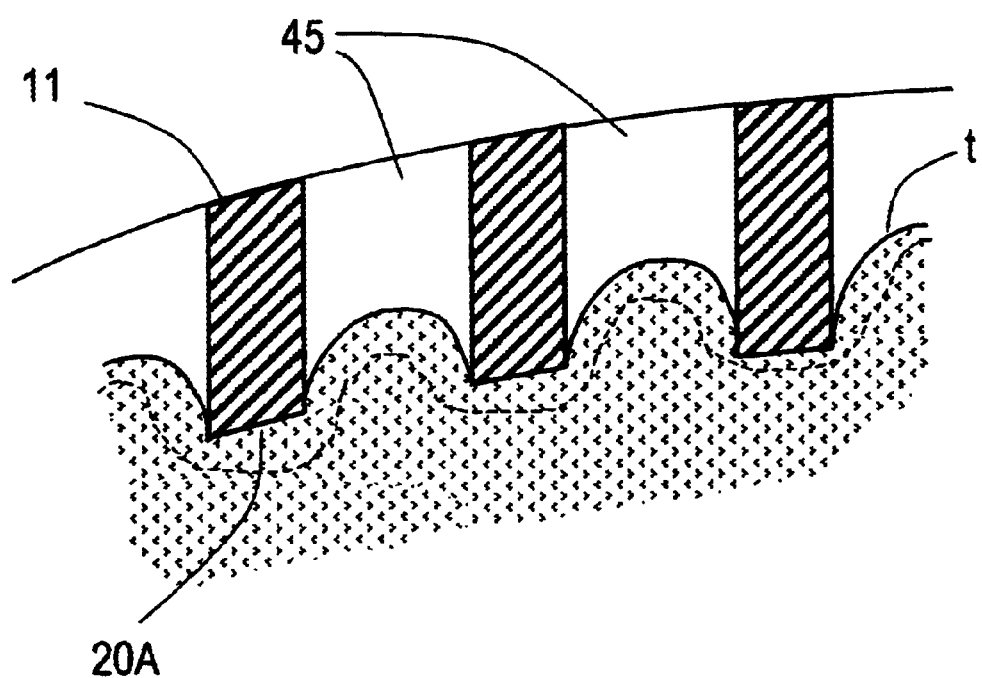

In another aspect of the method of the invention, the engaging surfaces 20A and 20B can provide controllable tissue-compression means that will assist in the fusion of the engaged tissue volume t. Referring to FIGS. 6A–6B, by defining a selected scale of the cross-sectional dimensions c of the apertures 45 and 50 in the engaging surfaces 20A and 20B, the invention provides controllable tissue-compression means for maintaining the targeted tissue t under the approximate desired pressures for causing tissue fusion. The cross-sectional dimension c is intended to represent a minimum side dimension of a rectangular aperture 45, or the diameter of a round aperture 50, as it is believed that the area of the aperture can be engineered to cooperate with a tissue surface s to optimize energy absorption. As can be seen in FIGS. 6A–6B, a targeted tissue volume t that is being treated or fused by the method of the invention is believed to undergo several stages in rapid succession. FIG. 6A shows a greatly enlarged sectional view of the step of capturing the targeted tissue t between the first and second engaging surfaces 20A and 20B before thermal energy delivery. FIG. 6B next depicts the effect of hydrothermal energy delivery in which collagen and other proteins denature as well as hydration of the targeted site t. The denaturation of collagen causes the unwinding of its helical molecular structure and results in an expanded volume of tissue. This protein denaturation and tissue hydration causes the tissue surfaces s to expand and swell in the directions of arrows ar into apertures 45 and 50 as shown in FIG. 6B. The targeted tissue t is unable to swell in the directions of arrows ar' since the tissue is constrained by the side portions 95a and 95b of the working end 10 (see FIG. 3 and FIG. 5A). By providing apertures in the engaging surfaces 20A and 20B of a selected dimension c, the tissue can be controllably allowed to swell or expand into the apertures 45 and 50. It is believed that overly high compression of tissues may be adverse to creating effective tissue fusion, as such compression may reduce the ability of denatured proteins and other tissue constituents to intermix and thereafter fuse uniformly upon healing. After a ramp down in temperature, the fused portion f of FIG. 6B will shrink from within the apertures 45. The invention provides tissue engaging surfaces 20A and 20B that carry a grid of apertures having a selected cross-sectional dimension ranging from about 0.2 mm. to 2.0 mm for receiving swelled tissue, and more preferably from about 0.4 mm. to 1.0 mm. Thus, the tissue-receiving apertures 45 and 50, by having selected dimensions that can act as a passive component of the invention to transiently receive swelled tissue in the ramp-up in temperature and hydration to slightly reduce tissue compression, and thereafter release the tissue m the ramp-down in temperature and swelling. It should be appreciated that such apertures or recessed portions of a selected dimension may be provided in the engaging surface of any jaw structure (e.g., any Rf electrode jaw) for achieving the purpose of this method.

Figure 7:
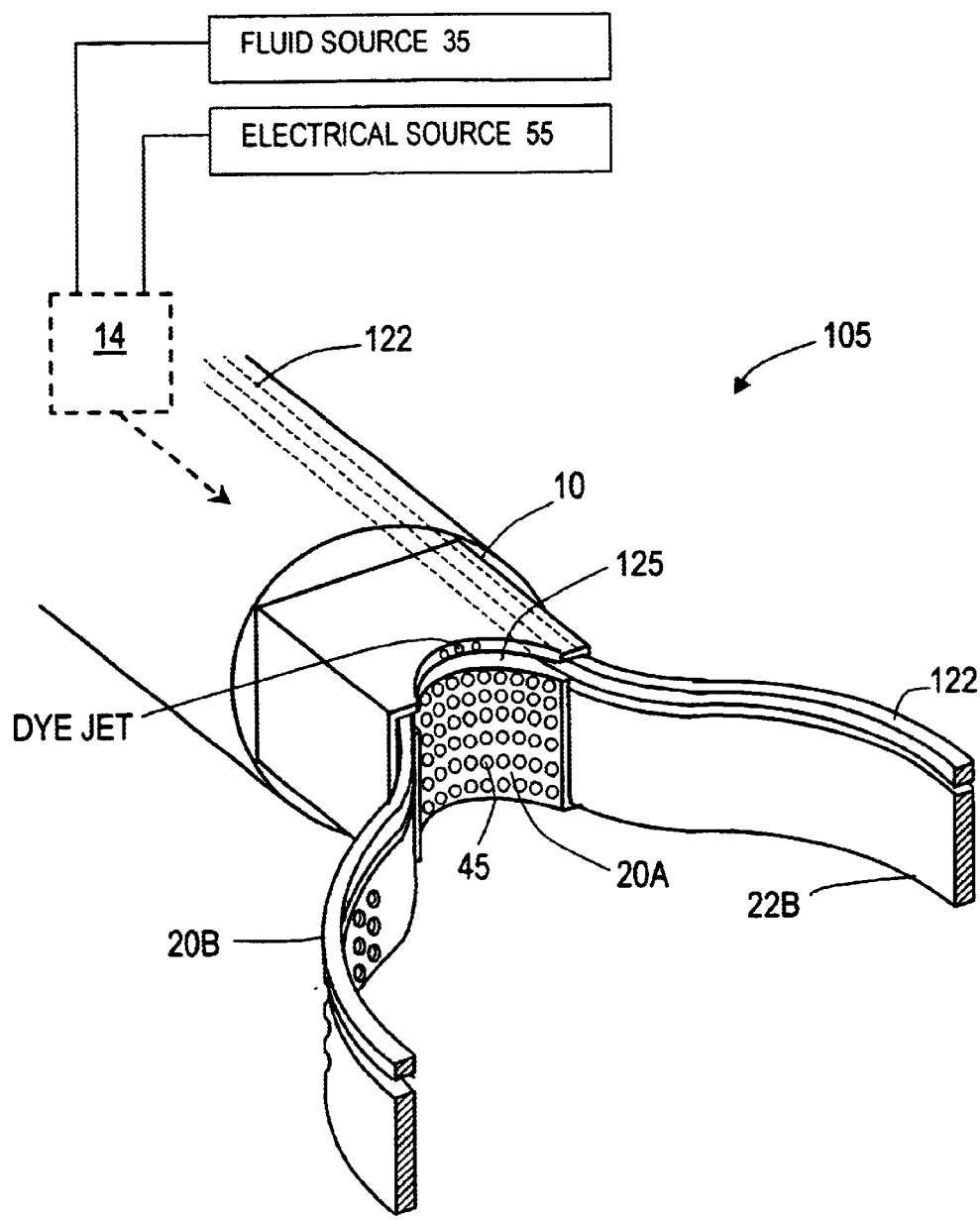
FIG. 7 is a perspective view of the working end of a Type "B" probe of the present invention with a loop type cutting electrode.

2. Type "B" System for Tissue Fusion and Resection. Referring to FIG. 7, an alternative working end 110 of a Type "B" system 105 of the present invention is shown. All energy delivery components of the Types "A" and "B" embodiments are the same and have similar reference numbers in the Figures. The Type "B" embodiment includes an additional functional component that comprises a cooperating tissue-cutting loop indicated at 122 in FIG. 7. The wire loop 122 may be round or square in section and is slidable in a separate channel 125 of the working end 110. The cutting loop 122 has as proximal portion 124 that extends to an actuator in the handle to pull the loop to transect captured tissue. Preferably, the loop is of conductive material and comprises a mono-polar electrode that is coupled to the electrical source 55 that provides cutting power as is known in the art. It can be understood that the cutting loop 122 can be actuated to electrosurgically transect the polyp adjacent to, or through, the fused tissue indicated at f (cf FIG. 5B). Thus, a single instrument (i) can seal the base of the polyp to prevent bleeding, and (ii) transect the head portion of the polyp for retrieval with another instrument.

Figure 8:
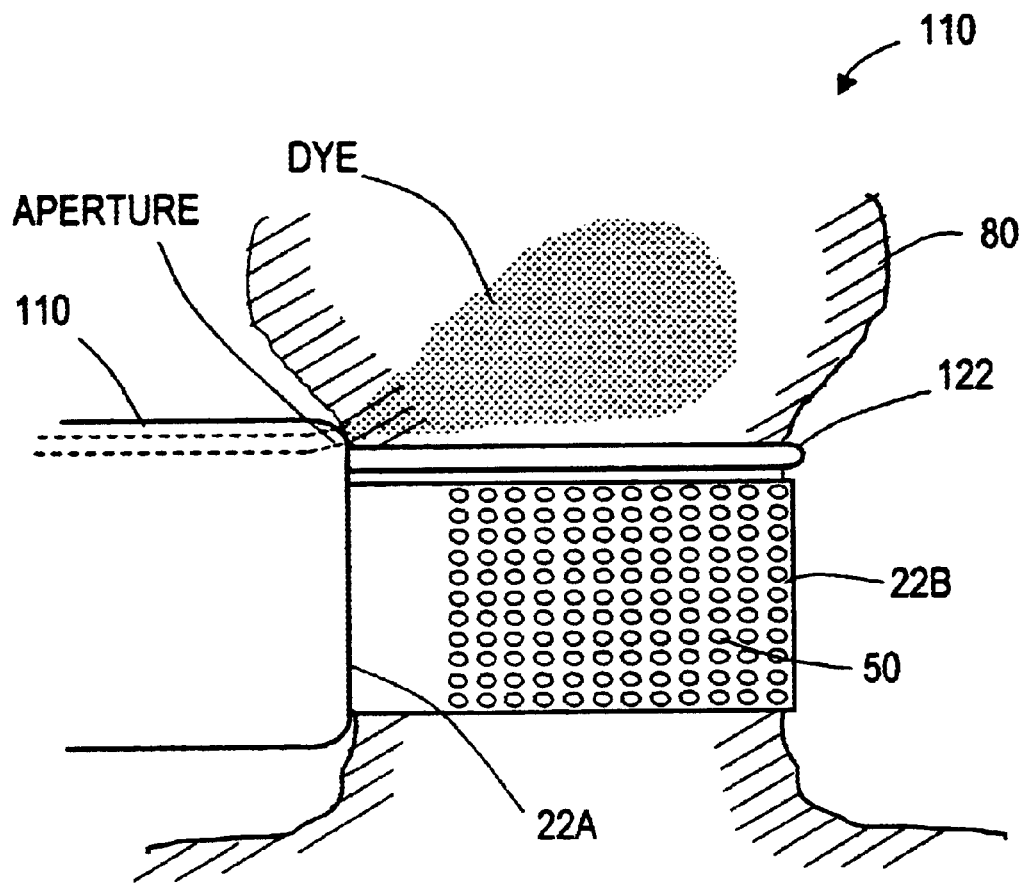
FIG. 8 is a sectional view of another embodiment of Type "B" working end.

An additional component may be added to the instrument and method of the invention that comprises a tissue-marking means. In the procedure illustrated in FIG. 8, the working 210 of the instrument may be advanced within the patient's colon to transect or resect several polyps. After the transections are completed, the transected polyps may be difficult to find and identify within the colon when a later instrument is used to retrieve the tissues for biopsy purposes. To make it easy to find the transected polyps, the fluid media m may be provided with any suitable surgical marking dye (e.g., isocynanine green dye, floreciene dye, or any other dye known in the art) and the dye pigment will penetrate a portion of the polyp to mark it for later visual identification. Since the dye will mainly penetrate the region targeted for fusion, another optional component of the invention is a separate set of apertures in surface 22A proximate to cutting loop 122 coupled to an independent fluid dye reservoir and pressure source (not shown) for marking the polyp head portion prior to its transection. Such apertures may be aligned to spray the dye somewhat laterally to strike the head portion of the polyp. The dye further may be any type of florescent dye that cooperates with a selected light wavelength introduced through the endoscope or working channel to locate the transected polyps.

Figure 9:
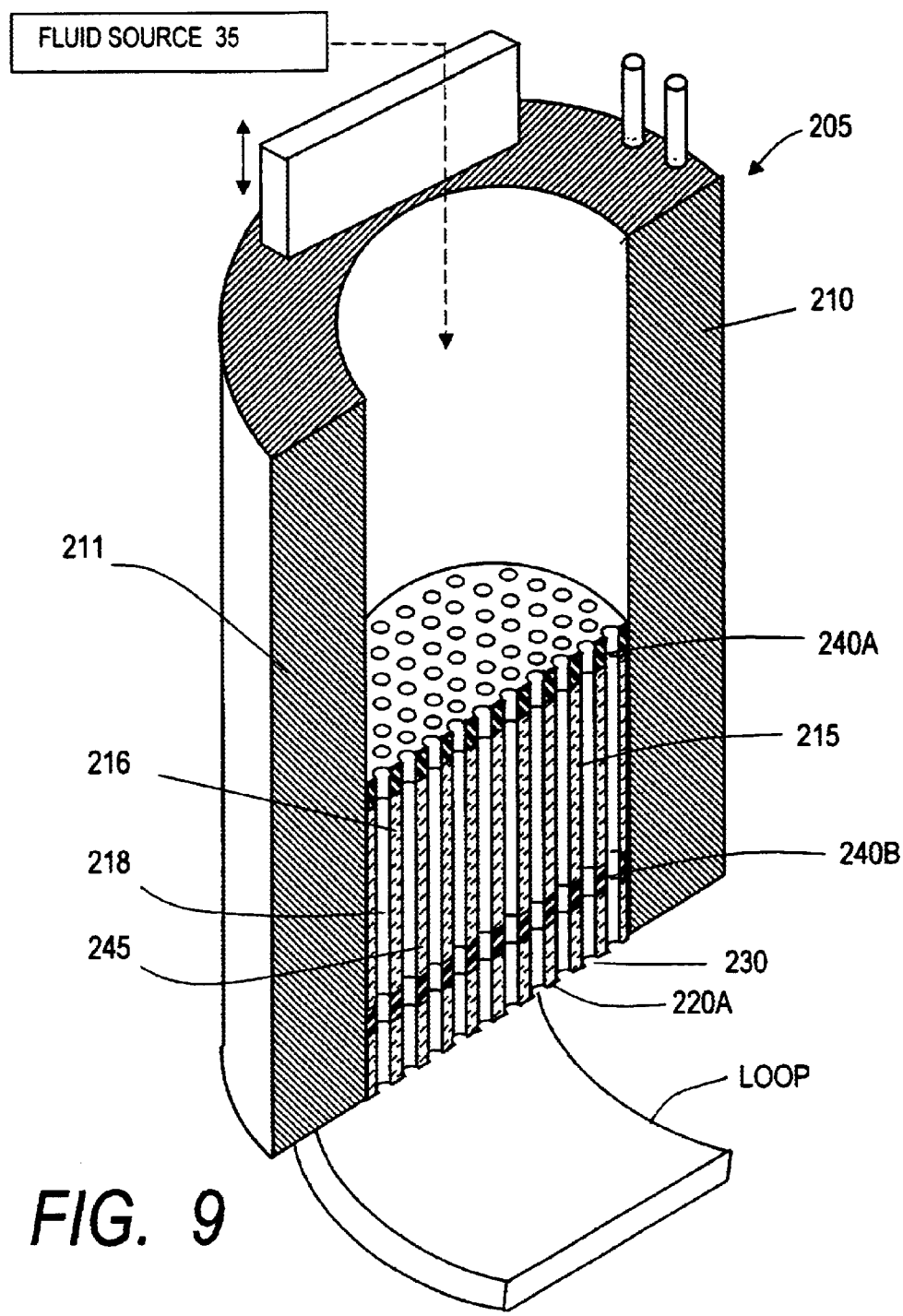
FIG. 9 is sectional views of an exemplary working end of a Type "C" probe of the present invention.

3. Type "C" System for Tissue Fusion and Method of Making Working End. Referring to FIG. 9, a working end 210 of a Type "C" system 205 of the present invention is depicted. The fluid-to-gas energy delivery aspects of the Types "A" and "C" systems are similar with the exception that the Type "C" system provides a significantly reduced dimensions (or micronization) of the features of the working end 210. More particularly, a source 35 of fluid media as described above is adapted to flow the media through the introducer body 211 and thereafter into a microchannel body 215 that defines a plurality of fluid or gas passageways or microchannel portions 230 (collectively).

The microchannel body 215 comprises a structure of an electrically insulative material that has a proximal layer portion 216, a medial layer portion 218 and a distal working surface 220A for interfacing the targeted tissue t. The plurality of open passageways or microchannels 230 can be identified as extending through the proximal and medial portions 216 and 218 and exiting the distal working surface 220A. Within the proximal portion 216 of the microchannel body 215 is a first electrode element 240A that may be formed in a plate or layer 242A that intersects the passageways 230. Thus, each channels has a first electrode surface 244a exposed therein. Similarly, the medial portion 218 of microchannel body 215 carries a second electrode element 240B that is formed in a layer 242B to provide a second electrode surface 244b exposed in the microchannels 230.

This Type "C" working end and microchannel body 215 can be fabricated in the following manners. The working surface 220A that carries the microchannel structure proximal thereto can be fabricated by the same processes as a micro-channel plate (MCP). The insulator material 245 of the working surface may be glass, plastic, ceramic, a form of silicon or any other suitable material. As an example of fabricating the microchannels, a microchannel plate (MCP) is a device that is commercially available for photo-detection purposes and may be adapted for use in the present invention. In an MCP, a tubular cladding glass is mechanically supported in its bore by the insertion of a rod of etchable core glass to produce a potential microchannel. The assembly is then pulled through an oven and drawn down in diameter to produce a microchannel (after the core is etched away). A plurality of such drawn-down assemblies then are stacked and drawn down through the oven until a selected diameter is achieved for the core. Thereafter, the assembly is fused together and the cores are etched away leaving the microchannel structure. While commercially available MCP's typically may have channels or capillaries ranging from about 5 $\mu$m and 25 $\mu$m in diameter, for photodetection purposes, it can be seen that any suitable diameter of channels can be fabricated by the above methods, and a preferred range is from about 0.2 $\mu$m to 400 $\mu$m in cross-section. More preferably, the range of cross sectional dimension is from about 0.5 $\mu$m to 200 $\mu$m. Another manner of fabricating the microchannel structure of the present invention is to use conventional semi-conductor processing methods to create both the microchannels and the electrode layers in an insulator material as is known in the art and in the MEMS field (microelectrical machining).

Figure 10:
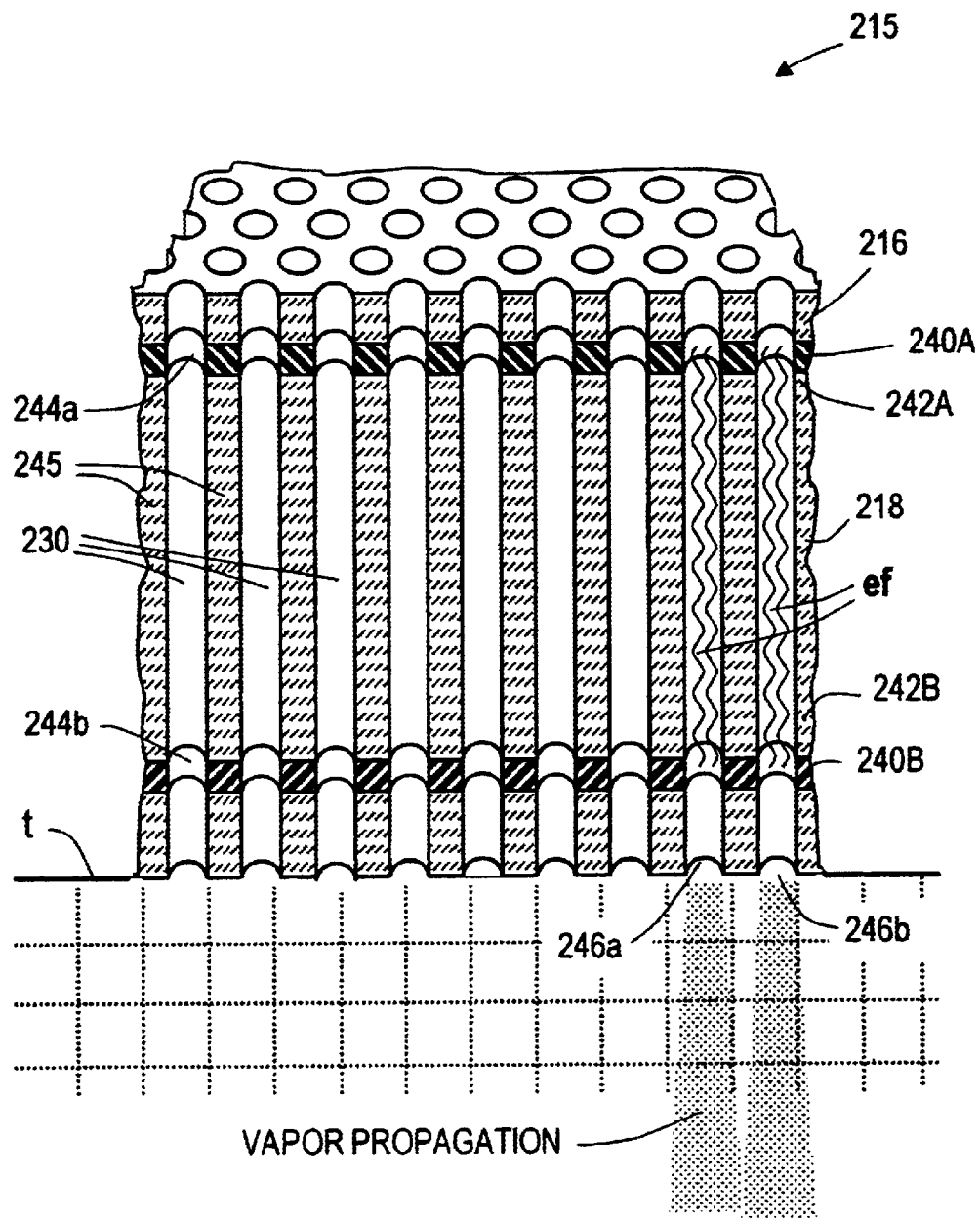
FIG. 10 is a greatly enlarged sectional view of the working end of FIG. 9 showing a microchannel structure and electrode arrangement carried therein.

In FIG. 10, an enlarged sectional view of a very small portion of the microchannel body 215 shows several microchannels 230 with open distal terminations 246a–246b in the working surface 220A. In any embodiment, the electrode layer indicated at 240A provides exposed surfaces 242a (collectively) that interface in a proximal portion of the microchannels. Similarly, the electrode layer 240B provides exposed surfaces 242b (collectively) that interface in a distal portion of the microchannels. It can be easily understood that for testing purposes, two MCP's can be sandwiched together to comprise the desired structure with a layer of insulator material 245 at the tissue engaging surface 220A. The distal electrode surface may be removed. Thus, the distal electrode exposed surfaces 242b are spaced inwardly or proximal from the distalmost working surface 220A a selected dimension that ranges from about 5 µm to 500 µm, in general varying in dimension in direct proportion with the cross-section of the channel and the voltage levels used. In other words, the electrode exposed surfaces 242b have a covering layer of insulator material 245 that prevents direct contact of any electrode with tissue in contact with the surface 220A. The method of using the Type "C" embodiment is substantially the same as the previously described to deliver a superheated gas media into targeted tissue, and need not be repeated. It can be easily understood that microchannel bodies 215 of the type shown in FIGS. 9–10 can be provided in one or both jaws of any type of tissue-engaging instrument.

The microchannel working end 215 of the type shown in FIGS. 9–10 can be provided in the alternative Type "C" embodiments of FIGS. 11A, 11B, 12A and 12B that are adapted for any thermotherapy in a targeted tissue t. For example, a probe 300 has an extension member 310 having a diameter of about 1.0 to 4.0 mm. (not limiting) that carries a microchannel structure in its working end as shown in FIGS. 9, 10, 11A & 12A. The distal working surface (engagement plane) of such a probe can engage the targeted tissue t by pressing the instrument against a tissue surface. The tissue targeted for such a thermotherapy may be any biological tissue, e.g., a patient's cornea, wherein a series of spots may be applied in a ring within the mid-stroma to shrink and reorganize collagen therein to alter corneal curvature. (A method of causing thermal effects in corneal tissue for similar purposes was disclosed utilizing other energy delivery means in co-pending U.S. patent applications Ser. No. 09/049,711 filed Mar. 27, 1998 and Ser. No. 09/174,366 filed Oct. 15, 1998, which are incorporated herein in their entirety by this reference).

Figure 11A:
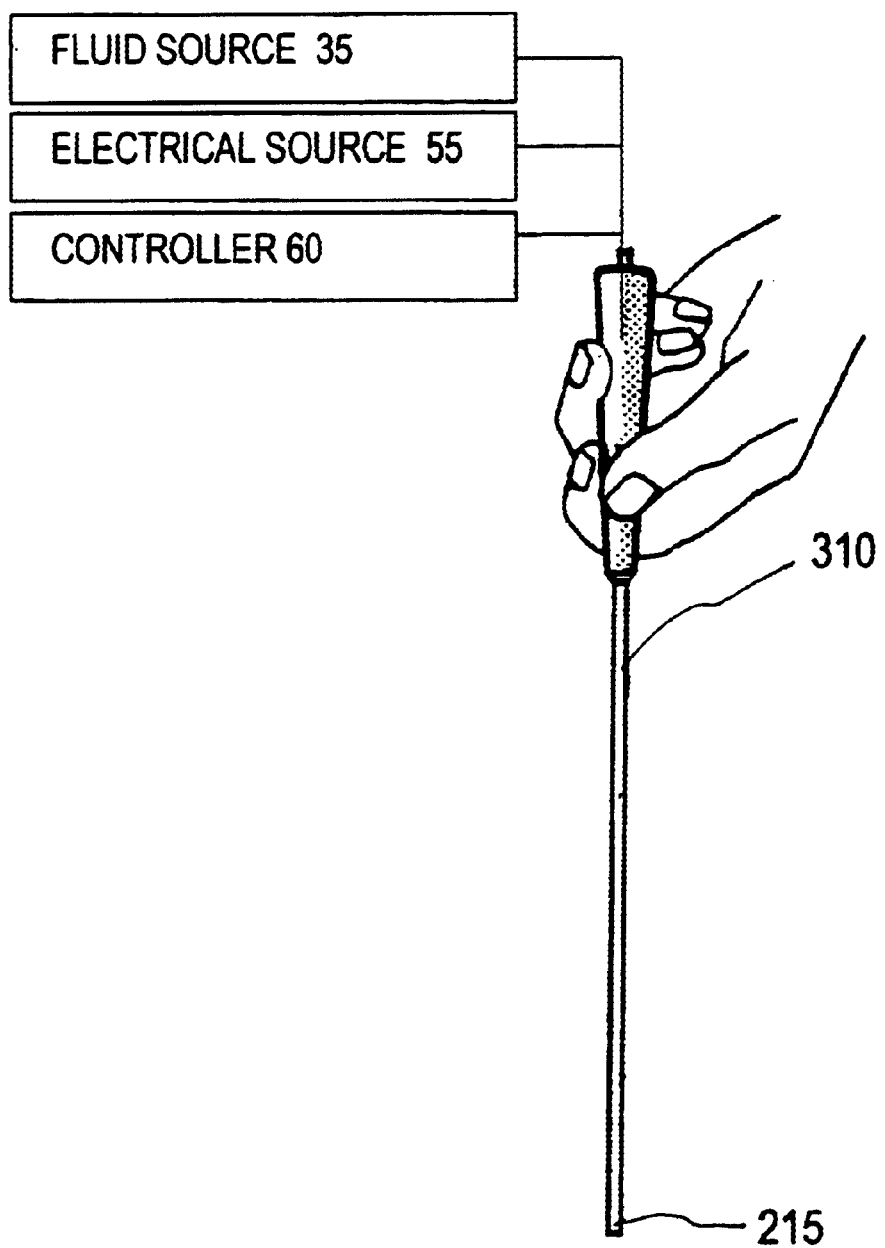
FIG. 11A is an alternative embodiment of Type "C" probe according to the present invention.
Figure 11B:
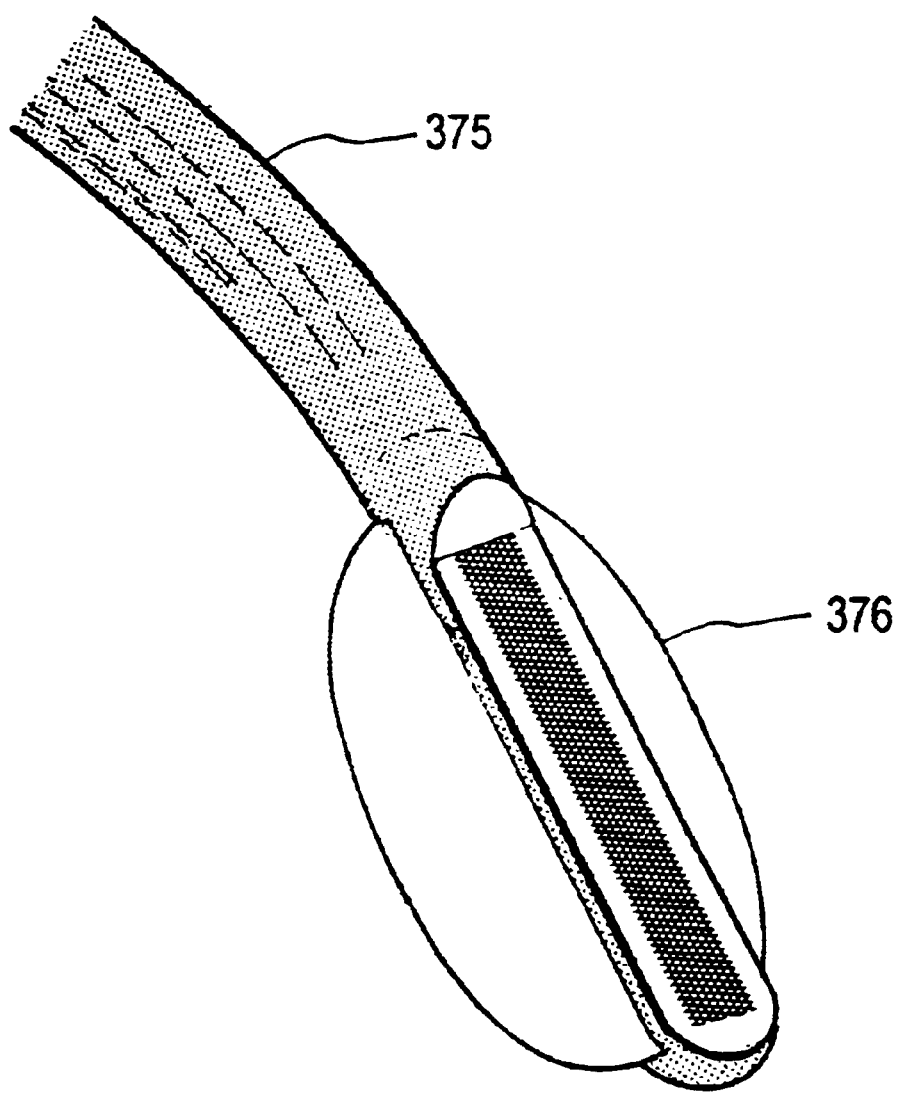
FIG. 11B is an alternative embodiment of Type "C" device comprising a catheter working end.

Such a Type "C" channeled structure in a working end also can be carried in the sidewall of a catheter that is from 1.0 to 3.0 mm in diameter (not limiting) as shown in FIG. 11B. The microchannel structure is oriented so that the heated fluid media is ejected transverse to the axis of the catheter 375. The targeted tissue t may be myocardium or other cardiac tissue in which it is desirable to create a linear weld, fusion or ablation in the tissue to alter electrical signal transmission in a treatment for atrial fibrillation as is known in the art. The catheter can be configured with a balloon 376 as is known in the art for positioning the working end in a treatment location. It is postulated that the method of the invention can create the desired elongate linear thermal effect in the targeted tissue with greater control over (i) the lateral margins of the treatment path, and (ii) the depth of treatment, when compared to prior art radiofrequency devices that deliver Rf energy that courses through the tissue in an unpredictable manner. A catheter may have with an optional expandable balloon for engaging an opposing wall of a cardiac structure to press the working surface against the targeted tissue t.

A Type "C" working end also may be used in orthopedic procedures to cause hydrothermal shrinkage of collagen, for example in a spinal disc, or a joint capsule to stabilize the joint (see co-pending U.S. patent application Ser. No. 09/049,711 filed Mar. 27, 1998, incorporated herein by this reference). For example, the working end may be painted across a targeted tissue site in a joint capsule to shrink tissue. The working end may be stabilized against any collagenous tissue to heat and shrink collagen in a targeted tissue such as a herniated disc.

The thermal energy delivery means of the invention preferably uses an electrical energy source for flash vaporization of a liquid media. It should be appreciated that an infrared laser source could be used to vaporize water or other lasers could be used to vaporize any other suitable fluid seeded with an absorbing biocompatible chromophore known in the art, and these embodiments fall within the scope of the invention.

Figure 12A:
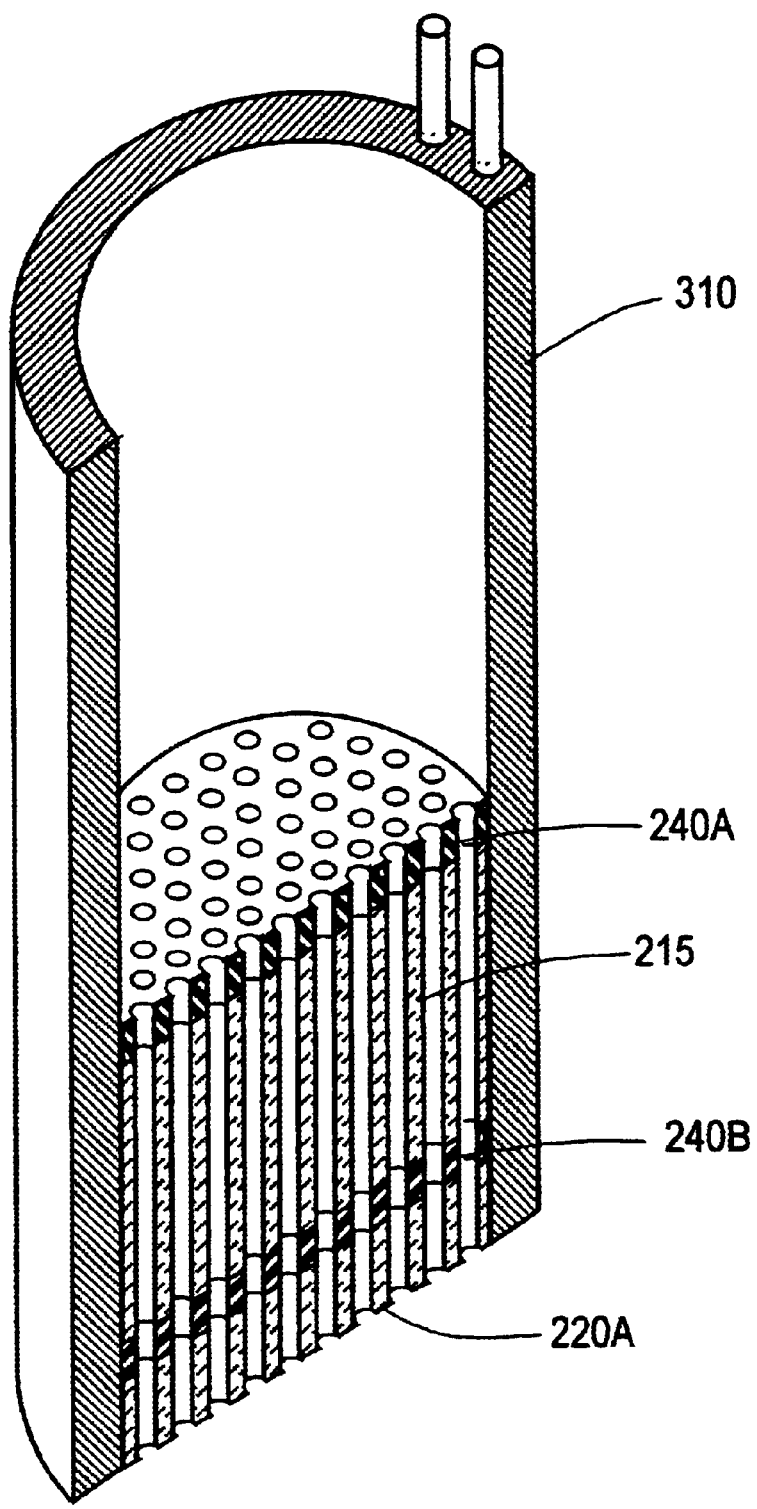
FIG. 12A is an enlarged sectional view of the working end of FIG. 11 showing a channeled structure and the electrode arrangement carried therein.
Figure 12B:
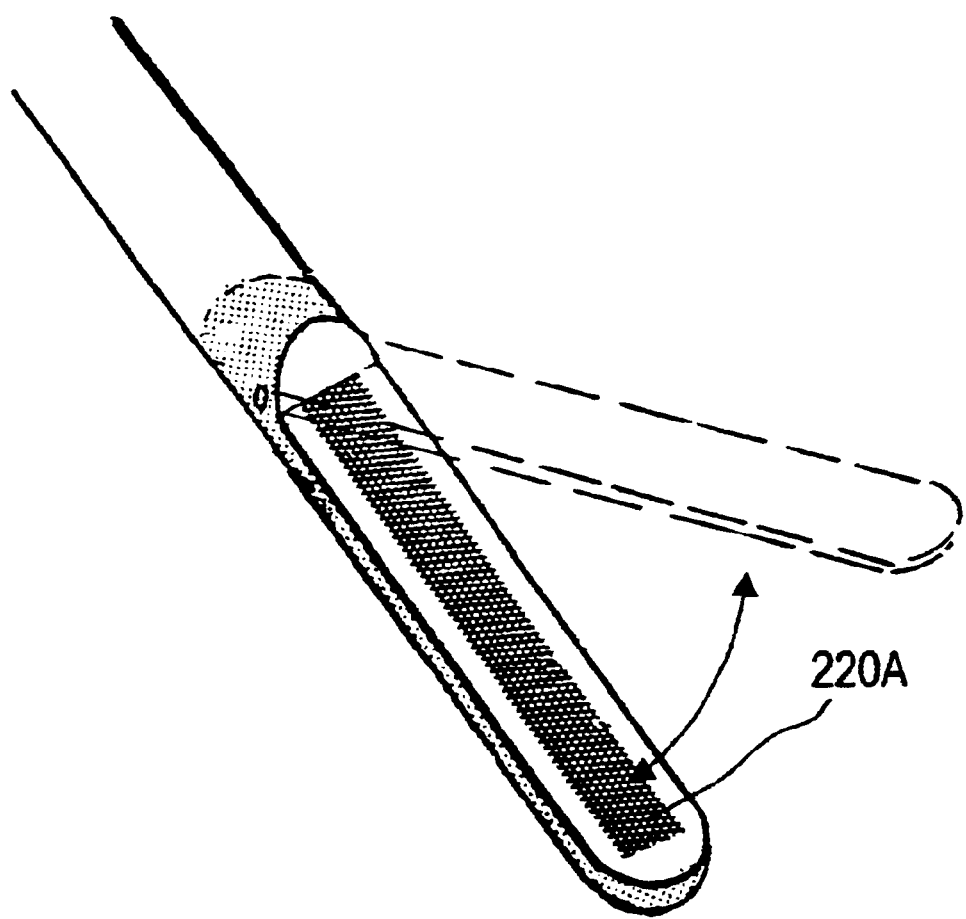
FIG. 12B is a perspective view of an alternative working end of a Type "C" embodiment with the working surface and channeled structure carried in a jaw of a tissue-engaging instrument.

It should be appreciated that the present invention has been described in detail in a particular embodiment suited for fusing or sealing a medial portion of a polyp prior to its resection. A similar working end may be used for capturing and fusing or sealing various other anatomic structures or tissue volumes in an endoscopic or open surgery. The working end of the instrument may be adapted to an open and closeable jaw structure to capture tissue as shown in FIG. 12B, rather than a "loop" to lasso tissue as in FIGS. 4A–4B.

Figure 13:
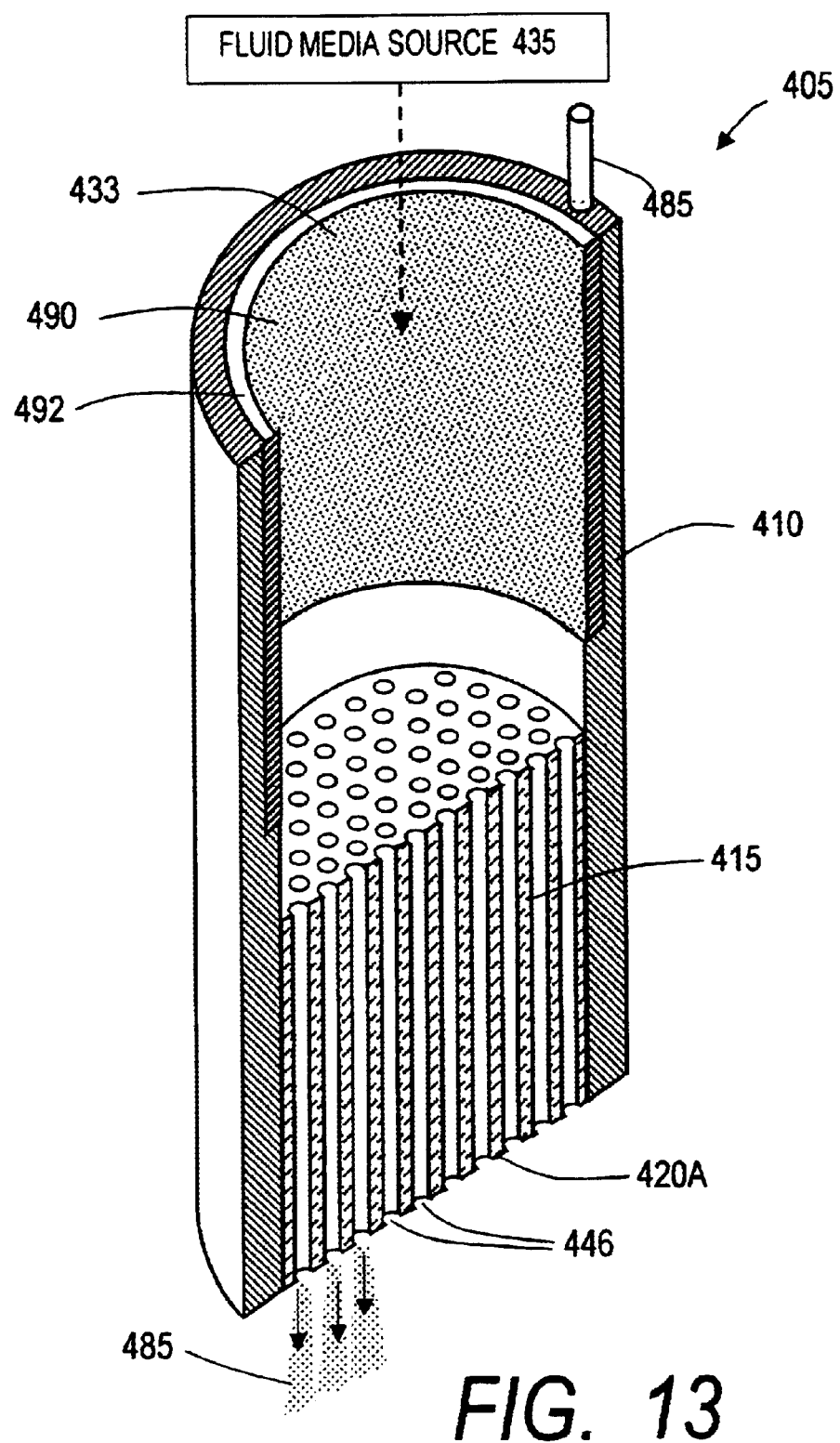
FIG. 13 is a perspective cut-away view of the working end of a Type "D" system with the working surface and channeled structure that utilize a high pressure fluid media inflow source and a resistive heating system.

4. Type "D" System for Thermotherapy of Biological Tissue. Referring to FIG. 13, a Type "D" system 405 of the present invention is depicted. A probe as shown in FIG. 11 carries working end 410 of FIG. 13. This system again defines an energy delivery interface 420A at the working surface of a channeled structure 415 having at least one channel 430 with an open port or orifice 446 in the interface 420A. The dimensions of the channels or porosities through the channeled structure 415 are the same as described previously.

The objectives of the Types "A" through "C" systems is to (i) cause high pressures in the working end to deliver high velocity flows of fluid media m from the energy delivery interface 420A to penetrate and interact with targeted tissue, and (ii) to impart a high temperature to the fluid media m before, or contemporaneous with, its ejection from the energy delivery interface 420A to thereby delivery energy to tissue.

Figure 14A:
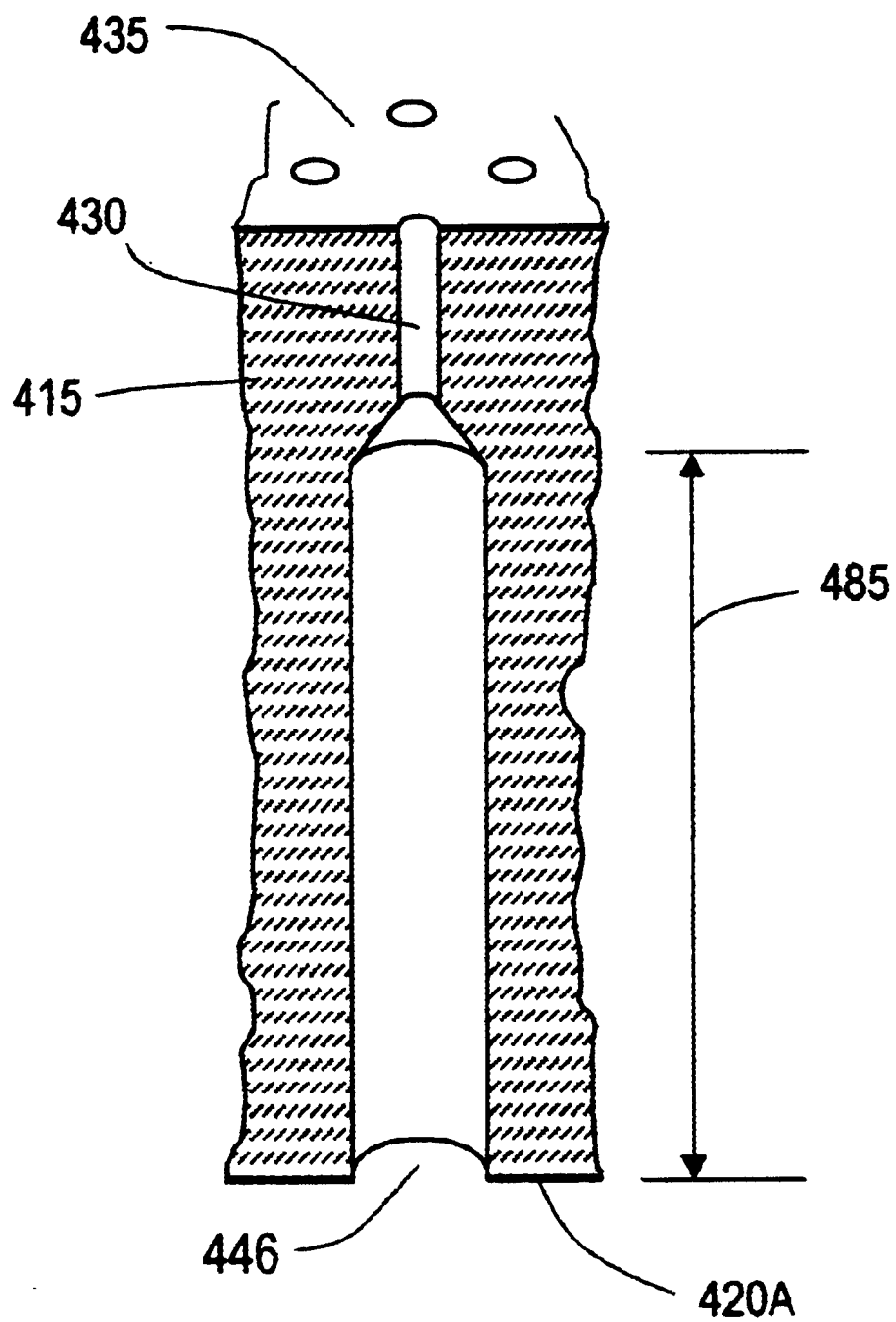
FIG. 14A is a sectional view of a single microchannel of an exemplary Type "D" working end.
Figure 14B:
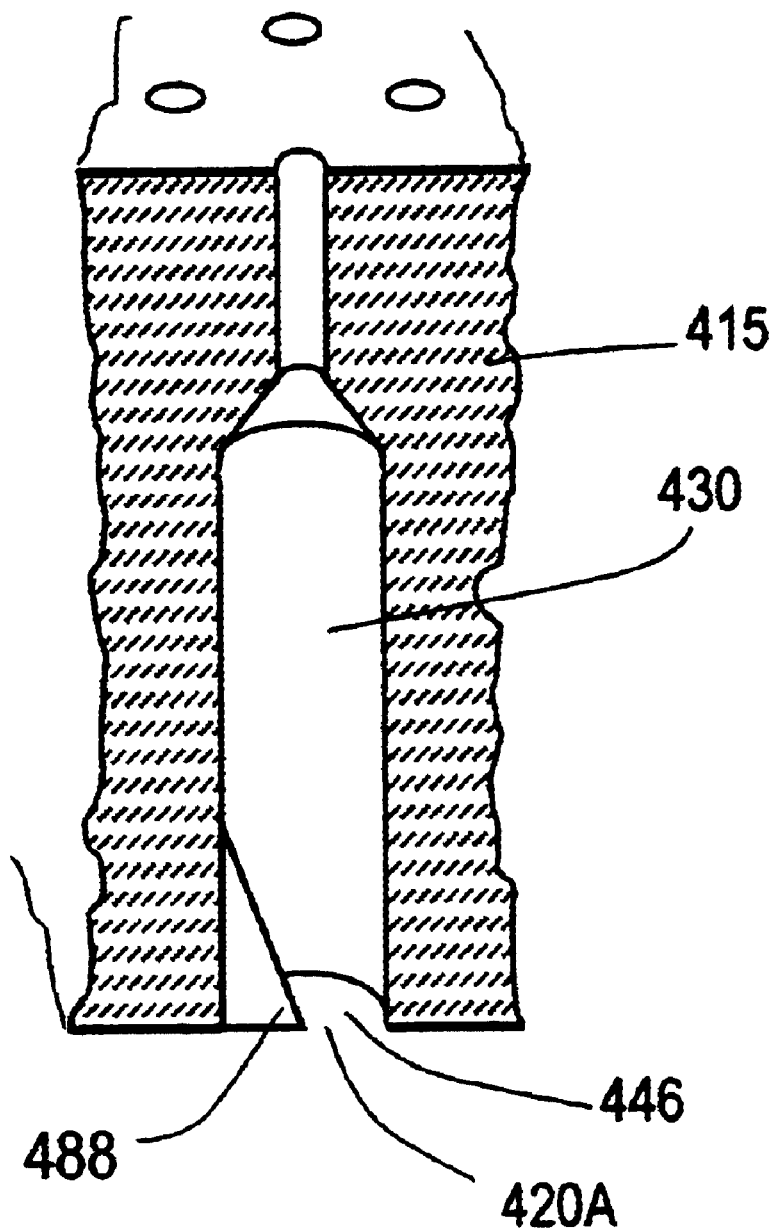
FIG. 14B is a sectional view of an alternative microchannel with a fluid deflecting structure.

The Type "D" system 405 according to the present invention is adapted to accomplish the two objectives described above by somewhat different means. The working end 410 provides a remote fluid media source 435 that can provide very high fluid pressures through interior channel 433 to the working end 410. The high pressure fluid source preferably is of the type described by the author in U.S. patent application Ser. No. 09/210,293 filed Dec. 11, 1998 titled Surgical Instrument For High-Pressure Fluid Debridement of Epithelial Layers, which is incorporated herein by reference. The pressure source preferably is adapted to provide extremely high fluid pressures and fluid jets at the surface 420A, for example ranging from 100 psi to 25,000 psi to essentially cause a fluid jet 485 as the flow exits the port or jet orifice 446 and is capable of cutting tissue. Depending on the selected velocity of the jetting effect, which is preferably pulsed, such a jet 485 can have a micron dimension cross-section or submicron dimension to thereby allow it to penetrate tissue to a selected depth to interact with tissue. As shown in FIG. 14A, the jet 485 also preferably is spaced apart from interface 420A a distance 428 ranging from about 100 microns to 5 mm. to allow the jet 485 to broaden it path and loose velocity. More preferably, as shown in FIG. 14B, the jet may be deflected off deflecting structure 488 to broaden its path and become a spray, which effect is described in U.S. patent application Ser. No. 09/210, 293.

The above-described system thus is adapted to accomplish one objective of the invention—that of creating high pressures in the working end to accelerate gas media flows from the engagement interface 420A. The other objective of the invention is to impart a high heat content to media m with a thermal energy delivery system 490 in the working end. In this embodiment, FIG. 13 shows that at least one conductive element 492 is coupled to an electrical source 455. In this embodiment, the at least one conductive element 492 is a resistive heating element 492 of any type as is known in the art cause very rapid conduction of heat to the fluid media passing through interior passageway 433 or the channels 430. Such a resistive heating element may be positioned along a lengthy portion of interior passageway 433 or within the channels and is shown positioned in passageway 433 for convenience.

Thus, this Type "D" embodiment can accomplish the objectives of (i) causing high pressures to deliver high velocity flows of fluid media m from an energy delivery interface 420A, and (ii) imparting high temperatures to the fluid media m before, or contemporaneous with, its jetting from the energy delivery interface 420A.

It should be appreciated that the thermal energy delivery system 490 can comprise paired electrodes to heat the fluid media m similar to the electrode arrangement shown in FIG. 3, or a combination of active and resistive electrodes may be used. Also a laser may be used for fluid vanorization as previously described. A microwave system known in the art also may be used.

In another embodiment, the combination of high pressures from a media inflow source 435 can be used together with fluid-to-gas means to create the desired pressures in the working end.

Figure 15:
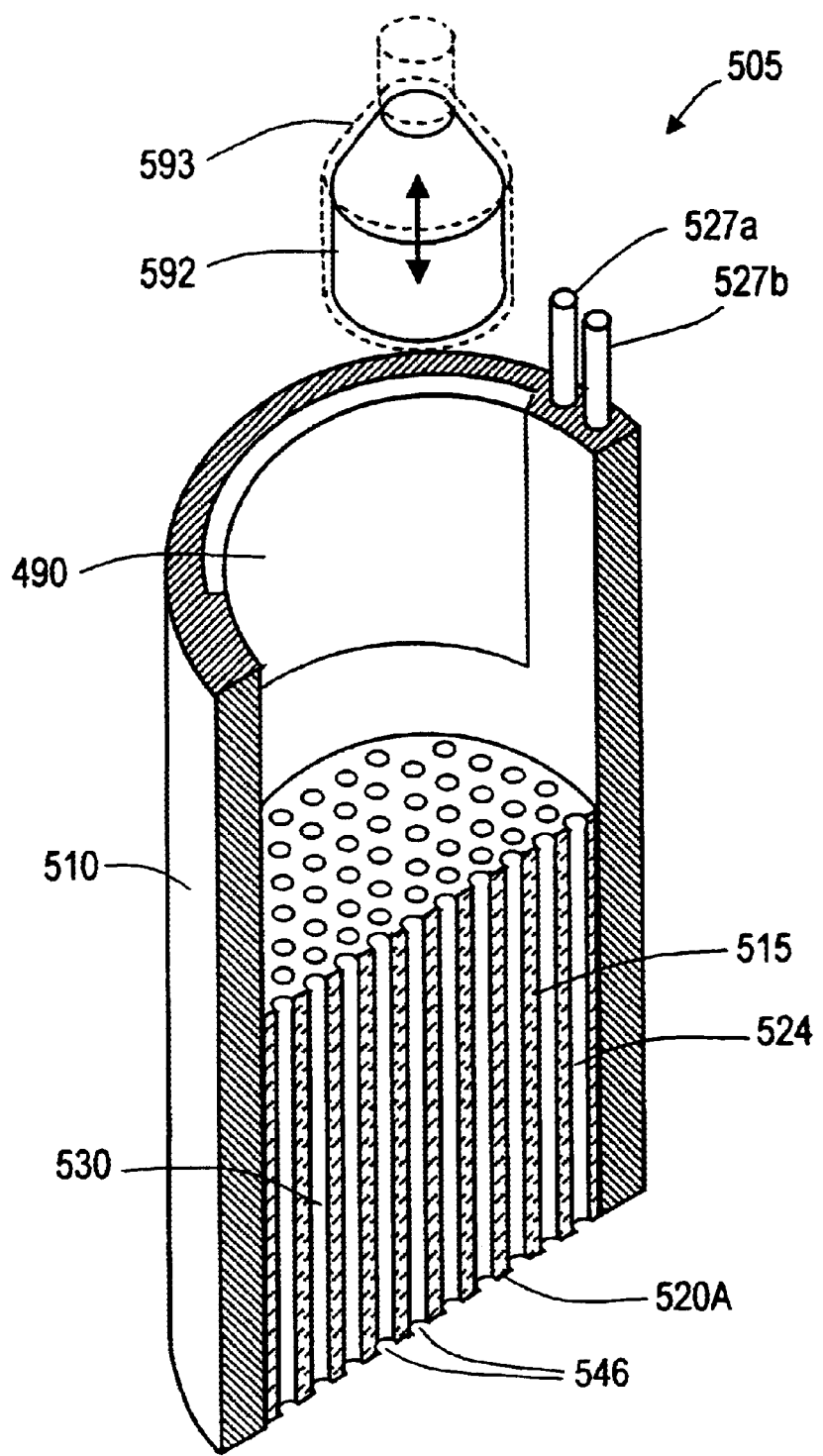
FIG. 15 is a perspective cut-away view of the working end of a Type "E" system with the working surface and channeled structure fabricated within a piezoelectric member.

5. Type "E" System for Thermotherapy of Biological Tissue. Referring to FIG. 15, a Type "E" system 505 of the present invention is depicted. The working end 510 of this system again defines an energy delivery interface 520A at the working surface of a channeled structure 515 having at least one channel 530 with an open port or orifice 546 in the interface 520A. The dimensions of the channels or porosities through the channeled structure 515 are described above.

The objectives of the Type "E" system of FIG. 15 are the same as described above in the Types "A" through "D" systems: (i) to cause high pressures in the working end to deliver high velocity flows of fluid media m from the energy delivery interface 520A to penetrate and interact with targeted tissue, and (ii) to impart a high temperature to the fluid media m before, or contemporaneous with, its ejection from the energy delivery interface 520A to thereby deliver energy to tissue.

This embodiment provides a novel means of accomplishing, or assisting in the accomplishment, of a first objective of the invention: the creation of high pressures in fluid channels of the working end to accelerate fluid flows from engagement interface 520A. The second objective of the invention in imparting a high heat content to the fluid media m with a thermal energy delivery system 490 can be any of the active electrode or resistive heating systems described above. Alternatively, a laser or microwave source may be used.

Of particular interest, the Type "E" embodiment of FIG. 15 shows a channeled structure 515 made of a piezoelectric material indicated at 524. Electrical leads 527a and 527b extend to the electrical source 555 and controller 580. As is known in the field of piezoelectric elements, electrical current flow to such a material causes mechanical forces in the material to thereby cause alteration of dimensional characteristics of the material. In this case, the piezoelectric material, the electrical current applied to the piezoelectric element, the repetition rate of electrical delivery and the cross-sectional dimension of the channels 530 in the piezoelectric channeled structure 515 are selected so that the cross-section of channels 530 can be controllably moved between a first greater cross-sectional dimension and a second lesser cross-sectional dimension to apply substantial pressure to the fluid media m within the channel. It can be understood that such pressure applied to the fluid media will force the fluid media outward of the channel to cause a transient high velocity flow from the en energy delivery interface 520A. Back pressure maintained by the fluid media source 535 can be used to insure the high velocity flow is ejected distally from surface 520A. Another preferred component of the invention is a back-pressure valve or one-way flow valve wherein moveable element 592 can move to and from in seat 593 (phantom view) as is known in the art to prevent any possible flow of fluid media m in the proximal direction caused by pressure applied to, or compression of, the fluid media m in the channels 530.

Figure 16:
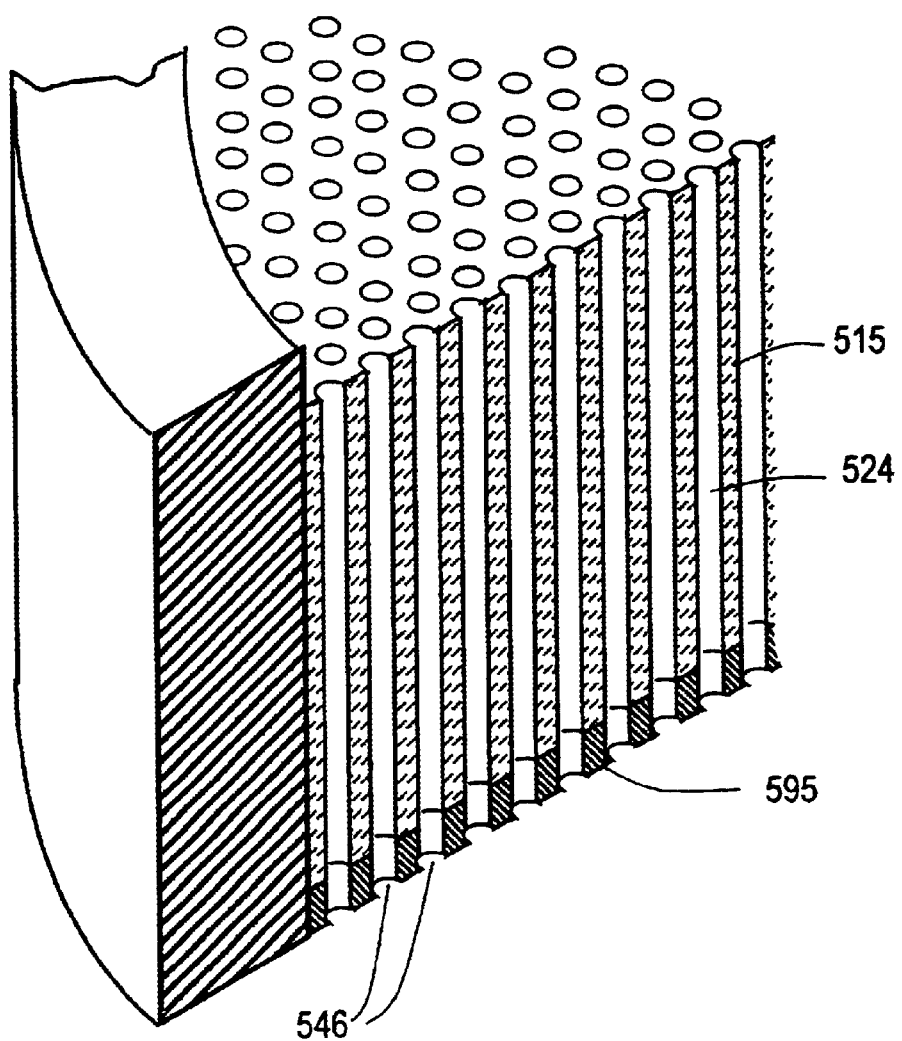
FIG. 16 is a perspective cut-away view of an alternative Type "E" working end with an electrode surface carried at the working surface of the piezoelectric member.

FIG. 16 shows another embodiment of a Type "E" working end wherein the piezoelectric channeled structure 515 carries active electrodes surfaces 595 at its energy delivery interface. The electrode surface 595 can be any thin electrically conductive coating applied to the piezoelectric element by thin layer metal coating methods known in the art. For example, Surmodics, Inc., 9924 West 74$^{th}$ Street, Eden Prairie, Minn. 55344 is skilled in surface coating techniques. This embodiment then would use the electrode surface 595 to deliver energy to tissue via the tissue's ohmic resistance (caused by current flow in tissue) in combination with the delivery of electrical energy to piezoelectric element to cause high velocity propagation of the fluid media into the targeted tissue t. The electrode surface 595 is shown as a mono-polar electrode to cooperate with a ground pad. k should be appreciated that conductive surface 595 optionally can comprise a resistive heating element as described above to conductive heat tissue. It should be further appreciated that conductive surface 595 can comprise a multiplicity of spaced apart conductive surface portions of any scale— including micron-scale islands—of opposing polarity that are coupled to the controller and electrical source 555 to provide bi-polar current flow. The use of a conductive surface 595 was disclosed in Provisional U.S. patent Ser. No. 60/230,556 filed Sep. 5, 2000 (Docket S-DESC-056) which is incorporated herein by reference. That disclosure also detailed the use of a channel structure as described above in the working end of a catheter for the creation of lesions in endocardial tissue. That disclosure also described the use of radiosensitive fluid agents which will not be repeated here.

It should be appreciated that such bi-polar flow can be used at low power for iontophoretic effects in delivering the fluid media m into the targeted tissue and fall within the scope of the invention.

The invention further includes the use of pharmacological agents within the fluid media, for example, to accelerate or decelerate neocollagenesis, which often is a factor related to the desired outcome of a thermotherapy. Such an agent may be CTGF (connective tissue growth factor) to cause neocollagenesis. Additionally, any pharmacological agent disclosed in the author's co-pending U.S. patent Ser. No. 09/615,221 filed Jul. 13, 2000 (Docket S-ECI-005B) titled *Electric Charge Induced Momentum Injection of Therapeutic Particles*, which is incorporated herein by this reference.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A method for a localized thermally-mediated therapy in a patient's body, comprising the steps of:
   (a) providing an instrument with an engagement surface at the distal end of an instrument body;
   (b) introducing a liquid media to at least one interior chamber in the interior of the instrument body;
   (c) utilizing a thermal energy deliveiy mechanism within said at least one interior chamber to vaporize the media; and
   (d) utilizing a pressurizing mechanism to cause the pressurized vaporized media to be ejected from openings in the engagement surface to apply energy to the patient's body.

2. The method of claim 1 wherein the thermal energy delivery mechanism of step (c) is selected from the class consisting of spaced apart electrodes coupled to an electrical source, a resistive electrode coupled to an electrical source, a laser source coupled to an emitter, and a microwave source coupled to an antenna.

3. The method of claim 1 wherein pressurizing mechanism of step (d) is selected from the class consisting of spaced apart electrodes coupled to an electrical source for causing vaporization of said media to cause increased pressure, a resistive electrode coupled to an electrical source for causing vaporization of said media to cause increased pressure, a laser source coupled to an emitter for causing vaporization of said media to cause increased pressure, and a piezoelectric element about said at least one channel coupled to an electrical source for causing compression of the fluid media within said at least one channel.

4. The method of claim 1 wherein step (c) vaporizes the liquid media by intense electrical energy delivery.

5. The method of claim 4 wherein step (d) includes causing the media to exit the engagement surface at a substantially high velocity.

6. The method of claim 1 wherein said thermally-mediated therapy is selected from the class comprising tissue welding, tissue sealing, hemostasis, causing a lesion in the tissue, and causing shrinkage of collagen in the tissue.

7. A medical device for delivering energy to the interior of a patient's body, comprising:
   a device with an engagement surface that defines at least one media port therein;
   a source of liquid media fluidly coupled to said at least one media port; and
   a thermal energy delivery mechanism intermediate to the source and the at least one media port and interior of the engagement surface for vaporization of the liquid to provide a volume of vapor ejecting from the at least one media port.

8. The device of claim 7 wherein the thermal energy delivery mechanism is selected from the class consisting of spaced apart electrodes coupled to an electrical source, a resistive conductor coupled to an electrical source, a laser source coupled to an emitter, and a microwave source coupled to an antenna.

9. The device of claim 7 further comprising a fluid pressurizing mechanism intermediate to the media source and the at least one media port for causing a high velocity flow of said media from said port.

10. The device of claim 9 wherein the pressurizing mechanism is selected from the class consisting of spaced apart electrodes coupled to an electrical source for causing vaporization of said media to cause increased pressure, a resistive electrode coupled to an electrical source for causing vaporization of said media to cause increased pressure, a laser source coupled to an emitter for causing vaporization of said media to cause increased pressure.

11. The device of claim 9 wherein the pressurizing mechanism comprises a piezoelectric element about said at least one channel coupled to an electrical source for causing compression of the fluid media within said at least one channel to thereby eject a high velocity flow therefrom.

12. The device of claim 7 further comprising a controller that causes a channel communicating with said at least one media port to move between first and second cross-sectional dimensions at a high repetition rate.

13. The medical device of claim 7 wherein said engagement surface is carried in a working surface of an endovascular catheter.

14. A medical device for delivering energy to a targeted tissue region, comprising:
   a device with an engagement surface for engaging tissue that defines at least one media entrance port therein;
   a source of media fluidly coupled to said at least one media entrance port for contact with the targeted tissue volume;
   a thermal energy delivery mechanism intermediate to the media source and the at least one media entrance port for elevating the temperature of the media to a range of vaporization thereof; and
   wherein said engagement surface is carried in a face of at least one jaw of a pair of cooperating jaw members that are openable and closeable to capture tissue.

15. An instrument for applying energy to an interior of a patient's body, comprising:
   an instrument body;
   an interior chamber in an interior of the instrument body for containing a fluid media;
   a pressurized fluid media source in fluid communication the interior chamber;
   at least one outflow channel extending to at least one outflow port in an insulated distal surface of the instrument body; and
   electrode means within the interior containment chamber for vaporizing the fluid media therein to provide a heated vapor for pressurized ejection from the at least one outflow port, wherein the interior chamber and electrode means are spaced apart from the insulated distal surface of the instrument body.

16. A method for causing thermal effects in targeted tissue, comprising the steps of:
   (a) engaging the targeted tissue with at least one engagement surface of an instrument working end;
   (b) propagating a gas media at a substantial velocity from at least one port in the engagement surface into the targeted tissue;

(c) wherein the gas media has a temperature within a selected range capable of denaturing proteins in the targeted tissue; and (d) wherein step (c) thereby transfers heat to the targeted tissue to create a thermal effects in the tissue.

17. The method of claim 16 wherein step (b) includes the step of creating the gas media volume from a liquid media in an interior region of the instrument by means of electrical energy delivery to the liquid media within the interior region to cause rapid vaporization, wherein the interior region is insulatively spaced avart from an insulated engagement surface.

* * * * *